(12) United States Patent
Matsumoto et al.

(10) Patent No.: US 9,399,788 B2
(45) Date of Patent: Jul. 26, 2016

(54) METHOD FOR INSPECTING SUSCEPTIBILITY OF BACTERIA OR FUNGI TO ANTIMICROBIAL DRUG AND SYSTEM FOR USE IN THE SAME

(75) Inventors: Yoshimi Matsumoto, Suita (JP); Kohei Hayama, Suita (JP); Shouichi Sakakihara, Suita (JP); Kunihiko Nishino, Suita (JP); Akihito Yamaguchi, Suita (JP); Hiroyuki Noji, Tokyo (JP); Ryota Iino, Tokyo (JP)

(73) Assignees: Osaka University, Osaka (JP); FUKOKU Co., Ltd., Saitama (JP)

(*) Notice: Subject to any disclaimer, the term of this patent is extended or adjusted under 35 U.S.C. 154(b) by 0 days.

(21) Appl. No.: 14/344,475

(22) PCT Filed: Aug. 31, 2012

(86) PCT No.: PCT/JP2012/072181
§ 371 (c)(1),
(2), (4) Date: Mar. 12, 2014

(87) PCT Pub. No.: WO2013/038925
PCT Pub. Date: Mar. 21, 2013

(65) Prior Publication Data
US 2014/0349333 A1 Nov. 27, 2014

(30) Foreign Application Priority Data

Sep. 13, 2011 (JP) .................................. 2011-200036

(51) Int. Cl.
*C12Q 1/18* (2006.01)
(52) U.S. Cl.
CPC ...................................... *C12Q 1/18* (2013.01)
(58) Field of Classification Search
USPC ...................................... 435/32, 288.5, 288.7
See application file for complete search history.

(56) References Cited

U.S. PATENT DOCUMENTS

| | | | | |
|---|---|---|---|---|
| 6,645,737 | B2 * | 11/2003 | Farina et al. | 435/32 |
| 2002/0025537 | A1 | 2/2002 | Bylina et al. | |
| 2002/0155515 | A1 | 10/2002 | Farina et al. | |
| 2003/0082516 | A1 | 5/2003 | Straus | |
| 2003/0143580 | A1 | 7/2003 | Straus | |
| 2003/0170613 | A1 | 9/2003 | Straus | |
| 2005/0048599 | A1 | 3/2005 | Goldberg et al. | |
| 2006/0166184 | A1 | 7/2006 | Yasuda et al. | |
| 2007/0037225 | A1 | 2/2007 | Metzger et al. | |
| 2008/0241858 | A1 | 10/2008 | Metzger et al. | |
| 2009/0315987 | A1 | 12/2009 | Straus | |
| 2010/0136570 | A1 | 6/2010 | Goldberg et al. | |
| 2010/0248281 | A1 | 9/2010 | Straus | |
| 2011/0003306 | A1 | 1/2011 | Thrippleton et al. | |
| 2011/0212440 | A1 * | 9/2011 | Viovy et al. | 435/6.1 |
| 2012/0077206 | A1 | 3/2012 | Metzger et al. | |
| 2013/0130262 | A1 * | 5/2013 | Battrell et al. | 435/6.12 |
| 2013/0217063 | A1 | 8/2013 | Metzger et al. | |
| 2014/0273046 | A1 * | 9/2014 | Sauer-Budge et al. | 435/18 |

FOREIGN PATENT DOCUMENTS

| | | |
|---|---|---|
| CN | 1299878 | 6/2001 |
| CN | 101382490 | 3/2009 |
| EP | 1 544 287 | 6/2005 |
| EP | 1 432 786 | 7/2009 |
| EP | 2 184 346 | 5/2010 |
| EP | 1 428 018 | 6/2010 |
| EP | 2 311 934 | 4/2011 |
| EP | 1 502 101 | 11/2012 |
| JP | 8-103293 | 4/1996 |
| JP | 2004-081019 | 3/2004 |
| JP | 2004-520593 | 7/2004 |
| JP | 2005-518553 | 6/2005 |
| JP | 2007-020486 | 2/2007 |
| JP | 2008-523820 | 7/2008 |
| JP | 2009-210392 | 9/2009 |
| JP | 2010-213598 | 9/2010 |
| JP | 2011-523546 | 8/2011 |
| WO | 02/086054 | 10/2002 |
| WO | 03/022999 | 3/2003 |
| WO | 03/036290 | 5/2003 |
| WO | 03/073817 | 9/2003 |
| WO | 2005/027714 | 3/2005 |
| WO | 2006/066216 | 6/2006 |

(Continued)

OTHER PUBLICATIONS

Ehrlich D. et al. Paralel Imaging Microfluidic Cytometer. Methods in Cell Biology 102:49-75, Jul. 19, 2011.*
Kloth K. et al. Development of an Open Stand Alone Platform for Regenerable Automated Microarrays. Biosensors & Bioelectronics 24(7)2106-2112, Mar. 2009.*
Liu J. et al. In Situ Microarray Fabrication and Analysis Using a Microfluidic Flow Cell Array . . . Analytical Chemistry 81(11)4296-4301, 2009.*

(Continued)

*Primary Examiner* — Ralph Gitomer
(74) *Attorney, Agent, or Firm* — Hamre, Schumann, Mueller & Larson, P.C.

(57) ABSTRACT

The present disclosure describes a method capable of easily and rapidly inspecting the susceptibility of bacteria or fungi to an antimicrobial drug. The inspection method of the present disclosure is a method for inspecting susceptibility of bacteria or fungi to an antimicrobial drug using a micro-device having flow channels, including: incubating a mixture of the antimicrobial drug and a suspension to be inspected in the flow channels of the micro-device; and detecting bacteria or fungi derived from the suspension to be inspected in an observation area of the flow channels of the micro-device. The detecting step can be performed by detecting an increase or decrease in the number of or a change in shape of bacteria or fungi derived from the suspension to be inspected in the observation area by a microscope or the like.

20 Claims, 15 Drawing Sheets

(56) References Cited

FOREIGN PATENT DOCUMENTS

| WO | 2009/095258 | 8/2009 |
|---|---|---|
| WO | 2010/041231 | 4/2010 |
| WO | 2011/094577 | 8/2011 |

OTHER PUBLICATIONS

Gefen O. et al. Single Cell Protein Induction Dynamics Reveals a Period of Vulnerability to Antibiotics in Persister Bacteria. PNAS 105(16)6145-6149, Apr. 22, 2008.*

Matsumoto Y. et al. Simple and Rapid Determination of Antibiotic Susceptibility Using Microfluidic Device . . . International J Antimicrobial Agents 42:S99, 2013.*

Kanemitsu, et al., "Evaluation of a Fully Automated System (RAISUS) for Rapid Identification and Antimicrobial Susceptibility Testing of *Straphylococci*" Journal of Clinical Microbiology, vol. 43, No. 11, pp. 5808-5810, 2005.

Ishii, et al., "Evaluation of antimicrobial activity of β-lactam antibiotics by Etest against clinical isolates", Japanese Journal of Chemotherapy, vol. 50, No. 5, pp. 259-265, 2002—English Abstract on p. 265.

Matsumoto, et al., "Evaluation of Multidrug Efflux Pump Inhibitors by a New Method Using Microfluidic Channels", PLoS ONE, vol. 6, issue 4, p. e18547, 2011.

Okumura, et al., "Novel Method of Oxygen Potential Measurement with Multichannel Electrodes to Determine Respiration Minimum Inhibitory Concentration of Antibiotics to Bacterial Cells", Tokyo Jikeikai Medical Journal, vol. 119, No. 6, pp. 455-462, 2004—English Abstract on p. 455.

Kuroda, "Development for Rapid Drug Susceptibility Assays of *Candida* Species by Flow Cytometry Method", Medical Journal of Kinki University, vol. 25, No. 1, pp. 13-24, 2000—partial English translation.

Notification of Reasons for Rejection issued in corresponding Japanese patent application No. 2013-533608, dated May 12, 2015, 4 pages—with partial English translation.

First Notification of Reasons for Rejection issued in corresponding Chinese patent application No. 201280044700.X, issued by the State Intellectual Property Office of the People's Republic of China, dated Jan. 20, 2015, 11 pages—with a partial translation.

Iino, et al., "A microfluidic device for simple and rapid evaluation of multidrug efflux pump inhibitors", Frontiers in Microbiology, vol. 3, article 40, Feb. 2012, pp. 1-9.

Whitesides, et al., "Soft Lithography in Biology and Biochemistry", Annual Review of Biomedical Engineering, vol. 3, 2001, pp. 335-373.

Extended European Search Report issued in the corresponding European Patent Application No. 12832460.5 dated Mar. 18, 2015.

Office Action issued in corresponding Canadian Patent Application No. 2,848,559 dated Mar. 19, 2015.

\* cited by examiner

METHOD FOR INSPECTING SUSCEPTIBILITY OF BACTERIA OR FUNGI TO ANTIMICROBIAL DRUG AND SYSTEM FOR USE IN THE SAME

TECHNICAL FIELD

The present invention relates to a method for inspecting the susceptibility of bacteria or fungi to an antimicrobial drug, and a system for use in the method.

BACKGROUND ART

Recently, the number of drug-resistant bacteria has been increased. Thus, in order to select an effective antimicrobial drug, it has been really important to check the susceptibility of bacteria or fungi to an antimicrobial drug.

In order to inspect the susceptibility of bacteria and fungi, devices (systems) aimed at simplification and acceleration have been released (Non-Patent Document 1). However, these large systems are expensive. Moreover, in order to determine turbidity, these devices require bacteria to be grown until a resultant culture has a turbidity that can be determined. For example, in the case of bacteria with a low growth rate such as *Pseudomonas aeruginosa*, it requires 8 hours or more to grow bacteria at the earliest. Furthermore, examples of a method requiring no such device generally include a broth microdilution method, a method in which the MIC (minimum inhibitory concentration) is determined from an inhibitory zone formed in an agar medium after cultivation by a disc with a concentration gradient, and a disc method based on a Kirby-Bauer method (K-B method) (Non-Patent Document 2). However, these methods also require about 18 hours from the initiation of inspection to determination of susceptibility. Thus, further acceleration of the inspection is required.

PRIOR ART DOCUMENTS

Non-Patent Documents

Non-Patent Document 1: Kanemitsu et al., Journal of Clinical Microbiology, 2005, pp. 5808-5810

Non-Patent Document 2: Ishii et al., Japan Journal of Chemotherapy, 2002, pp. 259-265

SUMMARY OF INVENTION

Hence, the present invention is intended to provide a novel method capable of easily and rapidly inspecting the susceptibility of bacteria or fungi to an antimicrobial drug and an inspection system for use in the method.

In order to achieve the aforementioned object, the inspection method of the present invention is a method for inspecting the susceptibility of bacteria or fungi to an antimicrobial drug using a micro-device having a flow channel (a flow path), the method including: an incubating step of incubating a mixture of the antimicrobial drug and a bacterial suspension to be inspected in the flow channel of the micro-device; and a detecting step of detecting bacteria or fungi derived from the bacterial suspension to be inspected in an observation area of the flow channel of the micro-device.

The inspection system of the present invention is a system for inspecting the susceptibility of bacteria or fungi to an antimicrobial drug by the inspection method of the present invention, the system including: an incubation unit that incubates a micro-device having a flow channel containing a mixture of a bacterial suspension to be inspected and the antimicrobial drug; an image acquisition unit that acquires an image of an observation area in the flow channel of the micro-device; an information acquisition unit that acquires information on at least one of the number and the shape (form) of bacteria or fungi in the image; and a determination unit that determines susceptibility of bacteria or fungi derived from the bacterial suspension to be inspected to the antimicrobial drug on the basis of the information.

According to the present invention, the susceptibility of bacteria or fungi to an antimicrobial drug can be easily and rapidly checked by incubating a mixture of the antimicrobial drug and a bacterial suspension to be inspected in a flow channel of the micro-device and observing an observation area in the flow channel by a microscope or the like, for example. Moreover, according to the inspection system of the present invention, the inspection method of the present invention can be performed easily. Therefore, the present invention is really useful in clinical inspection, environmental testing, and the like. Specifically, in the clinical inspection, for example, an appropriate antimicrobial drug for bacteria and fungi to be inspected can be selected promptly. Thus, effects such as an improvement in lifesaving rate, a reduction in volume of an unnecessary drug to be used, and the like are expected, and in the long run, there is a possibility of suppressing an increase in the number of resistant bacteria.

DESCRIPTION OF EMBODIMENTS

Figure 1A:
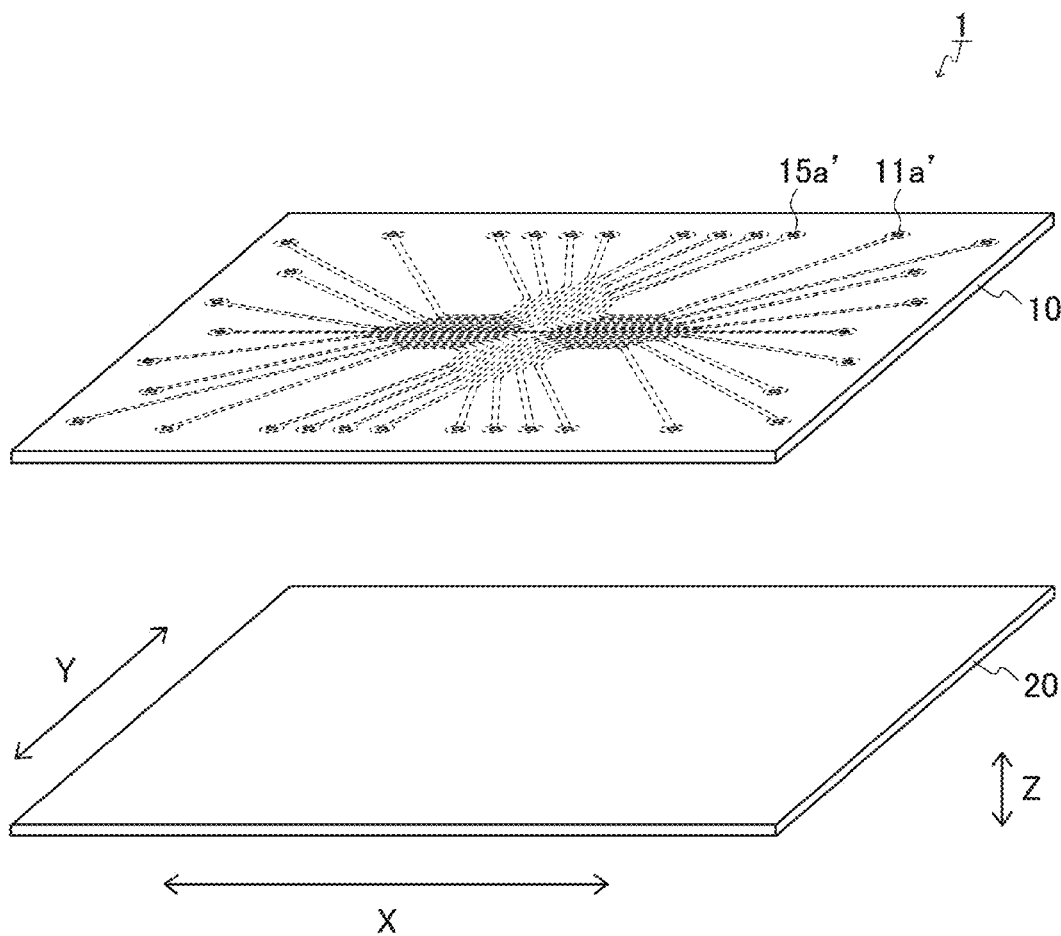
FIG. 1A is a perspective view showing an example of a micro-device.

The inspection method of the present invention is, as mentioned above, a method for inspecting the susceptibility of bacteria or fungi to an antimicrobial drug using a micro-device having a flow channel, the method including: an incubating step of incubating a mixture of the antimicrobial drug and a bacterial suspension to be inspected in the flow channel of the micro-device; and a detecting step of detecting bacteria or fungi derived from the bacterial suspension to be inspected in an observation area of the flow channel of the micro-device.

In the present invention, inspection of the susceptibility of bacteria or fungi to an antimicrobial drug encompasses inspection of a resistance of bacteria or fungi to an antimicrobial drug, for example.

In the inspection method of the present invention, the kinds of bacteria and fungi to be inspected are not particularly limited. Specific examples thereof include *Staphylococcus aureus, Enterococcus, Escherichia coli*, and other enteric bacteria, *Pseudomonas aeruginosa, Acinetobacter* bacteria and other sugar non-fermentable bacteria (which do not ferment sugar), *Streptococcus pneumoniae, Haemophilus influenza, Legionella* bacteria, *Campylobacter* bacteria, and *Mycobacterium tuberculosis*.

In the inspection method of the present invention, the kind of the bacterial suspension to be inspected is not particularly limited. The bacterial suspension to be inspected can be prepared from a colony obtained by isolation culture of a clinical specimen or the like, for example. The bacterial suspension to be inspected, however, is not limited by this, and for example, a clinical specimen as it is can be used. In this case, for example, the clinical specimen is preferably a specimen having a low probability of being contaminated and a specimen that can ensure a sufficient bacterial density. In the case of using the clinical specimen, for example, it is preferred that bacteria are extracted from the clinical specimen, and the extracted bacteria are re-suspended in a culture medium.

In the inspection method of the present invention, the structure of the micro-device is not at all limited as long as it includes a flow channel into which the bacterial suspension to be inspected can be introduced. Examples of the micro-device are described below.

In the inspection method of the present invention, the order of introducing the antimicrobial drug and the bacterial suspension to be inspected is not particularly limited. The introduction can be restated as inoculation or supply, for example. In the incubating step, for example, a mixture of the antimicrobial drug and the bacterial suspension to be inspected may be introduced into the flow channel of the micro-device. For example, the antimicrobial drug may be previously placed in the flow channel of the micro-device, and the bacterial suspension to be inspected may be introduced into the flow channel of the micro-device before or in the incubating step.

In the inspection method of the present invention, the volume of the bacterial suspension to be inspected and the number of bacteria in the bacterial liquid to be inspected (the density of the bacterial suspension) are not particularly limited. The volume and the density of the bacterial suspension can be set as appropriate according to the size of the micro-device, the size of the flow channel, and the like, for example. In the inspection method of the present invention, the volume of the antimicrobial drug to be used is not particularly limited and can be set as appropriate according to the volume of the bacterial suspension to be inspected, an estimated clinically effective concentration (breakpoint), and the like, for example.

In the inspection method of the present invention, the incubation conditions in the incubating step are not particularly limited. The incubation conditions can be selected as appropriate according to the optimal growth conditions of bacteria or fungi to be inspected, for example. The incubation temperature is not particularly limited and is, for example, from 30° C. to 37° C. As a specific example thereof, the incubation temperature of ordinary bacteria such as *Escherichia coli* and *Pseudomonas aeruginosa* is, for example, 37° C. The incubation time is not particularly limited, and the incubation time of bacteria with a high growth rate such as *Escherichia coli* is, for example, from 2 to 3 hours, and the incubation time of *Pseudomonas aeruginosa* and other sugar non-fermentable bacteria is, for example, from 3 to 4 hours. The incubation time, however, is not limited thereby, and the incubation can be finished when the growth of the bacteria to be inspected in the absence of the antimicrobial drug (control) reaches a level sufficient for determination, for example.

In the inspection method of the present invention, for example, this incubation time substantially becomes a factor for determining a total time required for inspection. Therefore, it can be said that, according to the inspection method of the present invention, the incubating step can be performed in a short time, and comprehensively, the inspection can be performed in a really short time.

In the incubating step, the micro-device is preferably incubated under the conditions where the humidity is maintained because the change in concentration of the antimicrobial drug caused by dryness in a flow channel by heating can be prevented sufficiently, for example. As a specific example, for example, it is preferred that the micro-device is incubated in an airtight container containing a tissue which contains water. The humidity is, for example, from 95% to 100%, preferably from 97% to 100%.

It is preferred that in the detecting step, at least one of an increase or decrease in the number of and the change in shape of bacteria or fungi derived from the bacterial suspension to be inspected in the observation area is observed, for example. In the detecting step, for example, at least one of the number and the shape or both of them may be observed. In the detecting step, for example, the degree of density of bacteria or fungi may be observed. In the detecting step, for example, changes in the number, shape, and/or the degree of density of bacteria or fungi before and after the incubating step or over time may be observed. In the case where bacteria or fungi show a resistance to the antimicrobial drug, when the incubation is performed, the number of the bacteria or fungi is increased, for example. On the other hand, in the case where bacteria or fungi show susceptibility to the antimicrobial drug, even if the incubation is performed, there is an indication that the number of the bacteria or fungi is not increased or is decreased by a bacterial death, or the shape is changed, for example. Thus, for example, susceptibility of bacteria or fungi to the antimicrobial drug can be determined by observing the increase or decrease in the number of bacteria or fungi and/or the change in shape. The susceptibility can be, for example, determined as the presence or absence of susceptibility or the MIC.

In the detecting step, detection method for detecting bacteria or fungi derived from the bacterial suspension to be inspected is not particularly limited and can be, for example, detection by a microscope. It is preferred that bacteria or fungi derived from the bacterial suspension to be inspected are detected by a microscope in the detecting step because the inspection can be performed more accurately. The kind of the microscope is not particularly limited, examples thereof include an optical microscope and a fluorescence microscope, and an optical microscope is preferable. The microscope is preferably a compact microscope, for example. The microscope preferably includes a CCD (Charge Coupled Device), for example. The inspection method of the present invention uses the micro-device and the microscope, so that it does not require the use of expensive devices (machines) and can avoid a requirement of a space by the devices, for example. Therefore, for example, the inspection method of the present invention easily can be introduced into existing inspecting rooms and laboratories and can be really easily performed. The detection by a microscope encompasses detection by an image output from the microscope, for example. The microscope is preferably linked to an output unit in order to obtain an image in the field of the microscope, for example. Examples of the output unit include a monitor and a printer.

In the detection method of the present invention, the detecting step is performed before or after the incubating step and is particularly preferably performed before and after the incubating step. That is, it is preferred that bacteria or fungi derived from the bacterial suspension to be inspected in an observation area of the flow channel is detected before and after the incubation of the micro-device. Thus, for example, the number of bacteria or fungi before the incubation and the number of bacteria or fungi after the incubation can be compared, or the shape before the incubation and the shape after the incubation can be compared, for example.

In the detection method of the present invention, the micro-device is not at all limited as mentioned above. The micro-devices are shown below as examples. The present invention, however, is not limited by the examples.

In the micro-device, the flow channel is not limited as long as a liquid can be moved inside the flow channel. The mechanism of causing a liquid to flow inside the flow channel is not at all limited. As a specific example, the liquid may be moved utilizing the capillary phenomenon of the flow channel or may be moved by pressurizing or depressurizing, for example. The flow channel is preferably a micro-flow channel, for example. For example, in order to ensure the length of the flow channel and the like, the flow channel may be provided in a bent state. In this case, for example, from the viewpoint of reducing a resistance to the liquid passing through the flow channel, a corner of the flow channel is preferably curved, round, or the like.

In the micro-device, one end of the flow channel is opened, for example. The opened end is, for example, an inlet of the bacterial suspension to be inspected and is also referred to as a supply port or an inoculation port. The other end of the flow channel also is preferably opened, for example. The other opened end is, for example, an air vent. The other opened end may be an outlet of leading out the bacterial suspension to be inspected which has been introduced from the inlet and has passed through the flow channel, for example. The outlet also can be referred to as a discharge port of discharging the bacterial suspension to be inspected from the flow channel, for example. In the flow channel, a direction of causing the bacterial suspension to be inspected to flow from the inlet is referred to as a "flowing direction". In the flowing direction, for example, the inlet side is the upstream side, and the air vent side is the downstream side. In the flow channel, the observation area is set to the downstream side from the inlet and is set between the inlet and the air vent, for example.

The flow channel further may have an exhaust section, for example. The exhaust section is preferably positioned on the downstream side from the observation area and is, for example, specifically positioned at the end of the flow channel. The exhaust section is, for example, an air vent. The end of the flow channel has an effluent section as an area in which the bacterial suspension to be inspected that has been passed through the observation area can be accumulated, for example. The end of the flow channel on the downstream side may have both of the exhaust section (air vent) and the effluent section.

Hereinafter, in the flow channel, the upstream side from the observation area is also referred to as an "introduction flow channel", and the downstream side from the observation area is also referred to as a "discharge flow channel". The length of the introduction flow channel may be identical to or different from the length of the discharge flow channel, for example. In the latter case, the discharge flow channel is preferably shorter than the introduction flow channel because air is supplied smoothly from the air vent (exhaust port), and bacteria or fungi derived from the bacterial suspension to be inspected can be easily grown, for example. The size of the observation area (e.g., width of the flow channel) may be identical to or different from the size of the introduction flow channel and the discharge flow channel (e.g., the width of the flow channel). In the latter case, even if the width of the flow channel is increased before and after the observation area from the viewpoint of reducing a resistance of the suspension, the size of the observation area is preferably smaller than the size of the introduction flow channel and the discharge flow channel in order to easily observe a plurality of flow channels by a microscope at the same time, for example.

In the micro-device, the flow channel is provided in a substrate (also referred to as a base material), for example. The substrate is preferably a transparent base material because it can be observed by a microscope or the like, for example. A raw material of the transparent base material is not particularly limited, and examples thereof include a polymer such as polydimethylsiloxane and glass. In the case where bacteria or fungi to be detected are aerobic bacteria or fungi, the substrate is preferably a breathable substrate.

In the micro-device, the substrate is preferably a laminate of an upper substrate and a lower substrate. For example, it is preferred that a concave portion as the flow channel is formed in the surface of the upper substrate on which the lower substrate is laminated, and the upper substrate has a through hole(s) at the position(s) corresponding to one end or both ends of the flow channel. By laminating the upper substrate and the lower substrate, for example, in a resultant laminate, a space formed by the concave portion of the upper substrate becomes the flow channel, and the through hole at the one end of the upper substrate becomes an inlet of the flow channel, and the through hole at the other end becomes an air vent (outlet) of the flow channel. A desired portion in the flow channel can be set as the observation area. When a liquid is supplied from the inlet of the upper substrate to the laminate, the liquid is introduced into the flow channel through the inlet, passes through the flow channel, and reaches the other end of the flow channel. The same applies to the case where the micro-device further includes the exhaust section. It is preferred that a concave portion as the exhaust section is further formed at the end on the downstream side of the flow channel in the surface of the upper substrate or the lower substrate, on which the lower substrate or the upper substrate is laminated. Moreover, it is preferred that the upper substrate has a through hole as the air vent at the position corresponding to the exhaust section, for example. The micro-device, however, is not limited by such form, and for example, the lower substrate may have the above-mentioned concave portion.

In the micro-device, for example, an antimicrobial drug may be previously placed in the flow channel. Hereinafter, in the flow channel, the portion in which the antimicrobial drug is placed or the portion on which the antimicrobial drug has been placed is also referred to as a reagent section. In the reagent section, an antimicrobial drug may be previously placed or may be placed in use before introduction of the bacterial suspension to be inspected, for example. In this case, for example, by supplying the bacterial suspension to be inspected to the micro-device, the bacterial suspension to be inspected and the antimicrobial drug can be mixed in the flow channel.

A method for placing the antimicrobial drug in the reagent section is not particularly limited, and for example, the antimicrobial drug can be placed by supplying an antimicrobial drug solution containing the antimicrobial drug to a desired portion of the flow channel and drying the antimicrobial drug solution. The antimicrobial drug may be placed in the flow channel by causing the antimicrobial drug solution to channel from the inlet or the outlet through the inside of the flow channel. It is preferred that the micro-device is dried after introducing the antimicrobial drug solution into the micro-device, for example.

In the case where an antimicrobial drug is previously placed in the micro-device, the micro-device is preferably stored in the dry state until the micro-device is used.

The micro-device may not include the reagent section, for example. In this case, for example, the bacterial suspension to be inspected and the antimicrobial drug are mixed outside of the micro-device, and this mixture may be introduced into the micro-device.

In the micro-device, the number of flow channels each having the observation area is not particularly limited. The number of flow channels can be set as appropriate according to the number of supplied bacterial suspensions to be inspected, the number of antimicrobial drugs, the number of concentrations of the antimicrobial drugs, the number of controls, and the like, for example. The number of flow channels each having the observation area is, for example, plural, two or more, for example, from 2 to 25. It is preferred that the number of the flow channels is set to the number capable of being placed in order to be easily observed by a microscope according to the purpose, for example. As described above, according to the micro-device having a plurality of the flow channels, it is possible to determine plural kinds of antimicrobial drugs, plural kinds of concentrations of the antimicrobial drugs, and/or plural kinds of bacterial suspensions to be inspected in one micro-device, for example. The number of the flow channels can be increased by increasing the size of the micro-device, for example. When the micro-device includes a plurality of the flow channels, the lengths of the flow channels may be identical to or different from one another. The former is preferable from the viewpoint of making the growth rates of bacteria or fungi derived from the bacterial suspensions to be inspected be even.

When the micro-device includes a plurality of flow channels, for example, it is preferred that, in the detecting step, bacteria or fungi derived from the bacterial suspension to be inspected in each observation area of the flow channels are detected. Moreover, in the micro-device, the observation areas of the plurality of flow channels are preferably parallel to and adjacent to one another and can be said to be placed in parallel, for example. In the case where a microscope is used in the detecting step, for example, it is preferred that all of the observation areas in the micro-device are converged and placed so as to be in a field of microscope because all of the observation areas can be observed by one observation.

When the micro-device includes a plurality of flow channels each having the observation area, the flow channels may be independent flow channels or may be partially linked with one another. The former micro-device is shown below as an example of the first embodiment, and the latter micro-device is shown below as examples of the second and third embodiments. The micro-device in the present invention, however, is not limited by these examples.

(First Embodiment)

A micro-device of the first embodiment is in a form of having different inlets and different observation areas in a plurality of flow channels, for example.

In the micro-device, for example, inlets and observation areas are separated from one another, and thus, in each observation area of the flow channels, inspections on a different bacterial suspension to be inspected, a different antimicrobial drug, and/or a different concentration of the same antimicrobial drug can be performed.

Figure 1B:
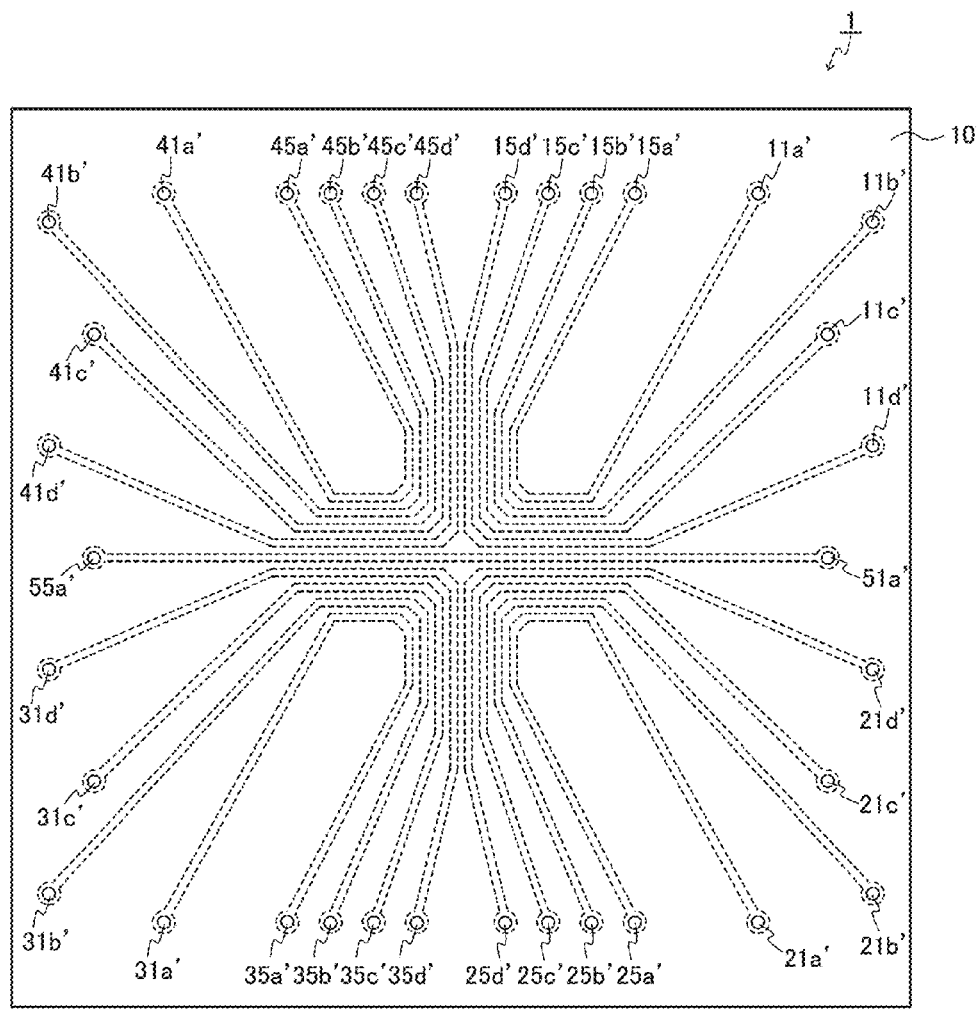
FIG. 1B is a top view showing the example of a micro-device.
Figure 1C:
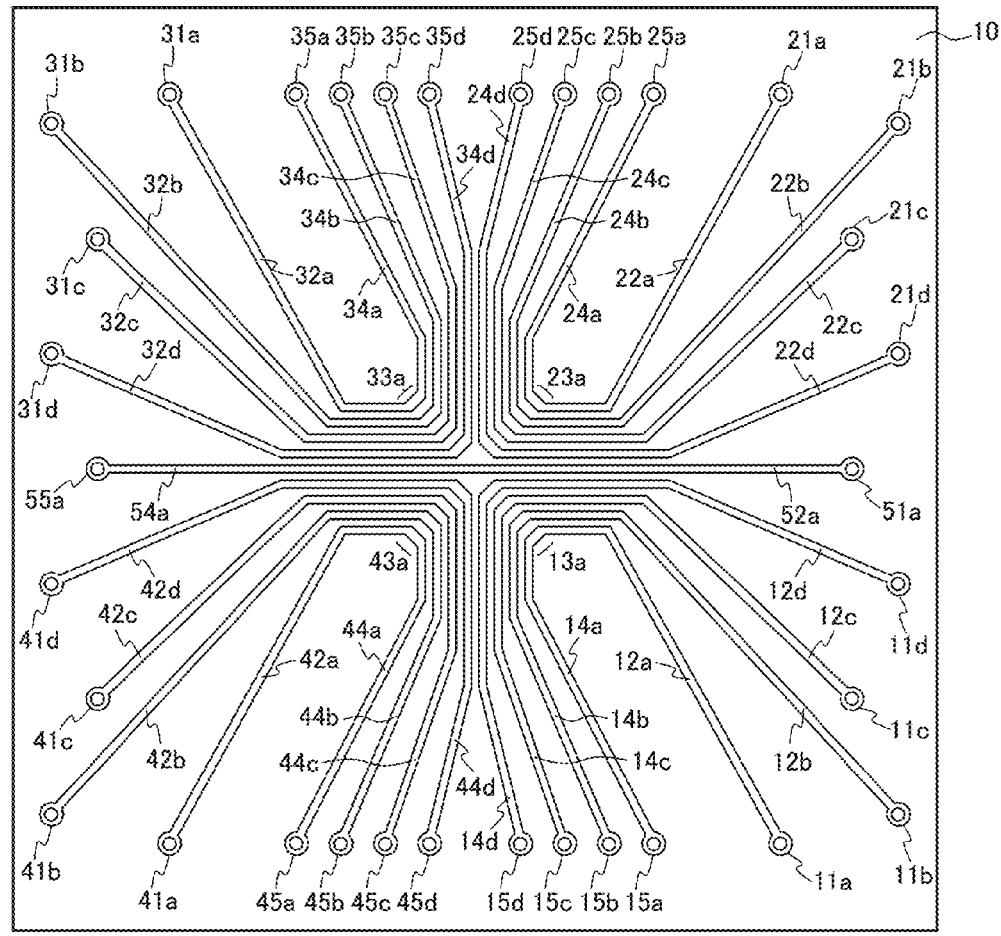
FIG. 1C is a bottom view showing an example of an upper substrate in the micro-device.

FIGS. 1A to 1C show an example of the micro-device. FIG. 1A is a perspective view showing a micro-device 1 in the state of separating into an upper substrate 10 and a lower substrate 20 which configure the micro-device 1. FIG. 1B is a top view of the micro-device 1. FIG. 1C is a bottom view of the upper substrate 10, i.e., a drawing of the surface of the upper substrate 10 on which the lower substrate 20 is laminated.

As shown in FIGS. 1A and 1B, an upper substrate 10 is provided with through holes 11a' to 11d', 21a' to 21d', 31a' to 31d', 41a' to 41d', and 51a' as inlets and through holes 15a' to 15d', 25a' to 25d', 35a' to 35d', 45a' to 45d', and 55a' as air vents. Although only the inlet 11a' and the air vent 15a' are three-dimensionally shown in FIG. 1A, the other through holes are the same.

As shown in FIG. 1C, in the lower surface of the upper substrate 10, introduction sections 11a to 11d, 21a to 21d, 31a to 31d, 41a to 41d, and 51a corresponding to the inlets 11a' to 11d', 21a' to 21d', 31a' to 31d', 41a' to 41d', and 51a', respectively, introduction flow channels 12a to 12d, 22a to 22d, 32a to 32d, 42a to 42d, and 52a, observation areas 13a to 13d, 23a to 23d, 33a to 33d, 43a to 43d, and 53a, discharge flow channels 14a to 14d, 24a to 24d, 34a to 34d, 44a to 44d, and 54a, and exhaust sections 15a to 15d, 25a to 25d, 35a to 35d, 45a to 45d, and 55a corresponding to air vents 15a' to 15d', 25a' to 25d', 35a' to 35d', 45a' to 45d', and 55a', respectively are linked respectively and formed as concave portions. Although the reference numerals of observation areas other than the observation areas 13a, 23a, 33a, and 43a are omitted in FIG. 1C, regions parallel to the observation area 13a are observation areas 13b to 13d in order from the observation area 13a side, regions parallel to the observation area 23a are observation areas 23b to 23d in order from the observation area 23a side, regions parallel to the observation area 33a are observation areas 33b to 33d in order from the observation area 33a, regions parallel to the observation are 43a are observation areas 43b to 43d in order from the observation area 43a, and a central region in the flow channel between the inlet 51a and the exhaust section 55a is an observation area 53a. The observation areas other than the observation area 53a are bent at two positions, and it is preferred that the portion parallel to the observation area 53a is observed.

Hereinafter, each space formed by linking the inlet, the introduction section, the introduction flow channel, the observation area, the discharge flow channel, the exhaust section, and the air vent is referred to as a "lane", and the name of each lane is represented by the reference numeral of each inlet. That is, for example, a space formed by linking an inlet 11a', an introduction section 11a, an introduction flow channel 12a, an observation area 13a, a discharge flow channel 14a, an exhaust section 15a, and an air vent 15a' is referred to as a lane 11a'.

The size of the micro-device 1 is not particularly limited and can be shown as follows, for example.

Overall Size
  Width (Length in an arrow X direction in FIG. 1A): e.g., 30 to 40 mm
  Length (Length in an arrow Y direction in FIG. 1A): e.g., 30 to 40 mm
  Thickness (Length in an arrow Z direction in FIG. 1A): e.g., 1 to 3 mm
Upper substrate 10,
  Thickness: e.g., 0.8 to 2.8 mm
  Depth of concave portion: e.g., 10 to 25 µm
Inlet
  Diameter: e.g., 0.75 to 1.5 mm, preferably 0.75 mm
Introduction Flow Channel
  Length: e.g., 10 to 15 mm
Observation Area
  Length: e.g., 1 to 5 mm
Discharge Flow Channel
  Length: e.g., 10 to 15 mm
Exhaust Section
  Diameter: e.g., 0.75 to 1.5 mm
Lower Substrate 20
  Thickness: e.g., 0.12 to 0.17 mm The micro-device may or may not have a reagent section, for example. In the former case, the position of the reagent section preferably includes at least the observation area, more preferably includes a range from the inlet to the observation area, yet more preferably includes a range from the inlet to the air vent, i.e., an entire flow channel including the introduction flow channel and the discharge flow channel, for example.

In the case where the antimicrobial drug is previously placed in the micro-device, for example, the antimicrobial drug solution is introduced from either one of the inlet and the air vent into the flow channel (the flow channel is filled with the antimicrobial drug solution), and thereafter, the micro-device is dried. Thus, the antimicrobial drug can be placed.

In the micro-device, the introduction volume of the antimicrobial drug solution into each lane is not particularly limited and is, for example, 0.2 to 3 µL per a lane. The preparation of the antimicrobial drug solution is not particularly limited, and for example, a solvent, the concentration, and the like can be decided as appropriate according to the kind of the antimicrobial drug. The solvent is not particularly limited, and examples thereof include ethanol, water, and a buffer solution.

In the micro-device, the introduction volume of the bacterial suspension to be inspected into each lane, is not particularly limited. In the micro-device, the introduction volume and density of bacteria in the bacterial suspension to be inspected into each lane is not particularly limited, and it is desired that the turbidity of the bacterial suspension to be inspected is adjusted to 0.5 McFarland, for example. The volume and density of bacteria in the bacterial suspension to be inspected can be modified according to the bacterial strain and the purpose of the inspection, for example.

Each flow channel of the micro-device has a different inlet. Therefore, according to the micro-device, for example, by introducing a bacterial suspension to be inspected containing a different antimicrobial drug into each flow channel, the susceptibility of specific bacteria to be inspected to a plurality of antimicrobial drugs can be checked. Moreover, according to the micro-device, for example, filling each flow channel with the same antimicrobial drug with a different concentration and introducing the same bacterial suspension to be inspected into each inlet, the MIC (minimum inhibitory concentration) of the specific antimicrobial drug can be determined. Furthermore, according to the micro-device, for example, by placing the same antimicrobial drug in each reagent section and introducing a different bacterial suspension to be inspected into each inlet, the susceptibility of each bacterial suspension to be inspected to the specific antimicrobial drug can be checked.

A specific example of the micro-device 1 can be, for example, in a form in which different antimicrobial drugs are placed in a group of lanes 11a' to 11d', a group of lanes 21a' to 21d', a group of lanes 31a' to 31d', and a group of lanes 41a' to 41d', the same antimicrobial drug with a different concentration is placed in each lane of each group, and the lane 51a' is used as a control of placing no antimicrobial drug. With this form, for example, the susceptibility and the resistance of one kind of a bacterial suspension to be inspected to each of four kinds of antimicrobial drugs can be checked. Furthermore, an antimicrobial drug with a different concentration is placed in each lane of each group, and thus, the MIC can be determined.

A method for inspecting susceptibility of a bacterial suspension to be inspected to a bacterial drug using the micro-device 1 having flow channels, each of which is filled with the bacterial drug, is shown below as an example.

First, the bacterial suspension to be inspected is supplied to each inlet in the micro-device 1. The bacterial suspension to be inspected, supplied to each inlet moves from the inlet to the flow channel and is thus mixed with the antimicrobial drug fixed in the flow channel.

Next, the micro-device 1 is incubated. The incubation conditions are, for example, as mentioned above. The observation area of the micro-device 1 is observed by a microscope to check the increase or decrease in the number of bacteria or fungi and the change in shape of the bacteria or fungi. Thus, the susceptibility to the antimicrobial drug can be inspected.

(Second Embodiment)

A micro-device of the second embodiment is in a form of having the same inlet and different observation areas in a plurality of flow channels, for example. The micro-device of the second embodiment can be described with reference to the description of the first embodiment unless otherwise specifically indicated.

In the micro-device, a plurality of flow channels have the same inlet, for example, and thus, in each observation area of the flow channels, inspections of the same bacterial suspension to be inspected on different antimicrobial drugs and/or inspections of the same bacterial suspension to be inspected on the same antimicrobial drug with different concentrations can be performed, for example.

Figure 2A:
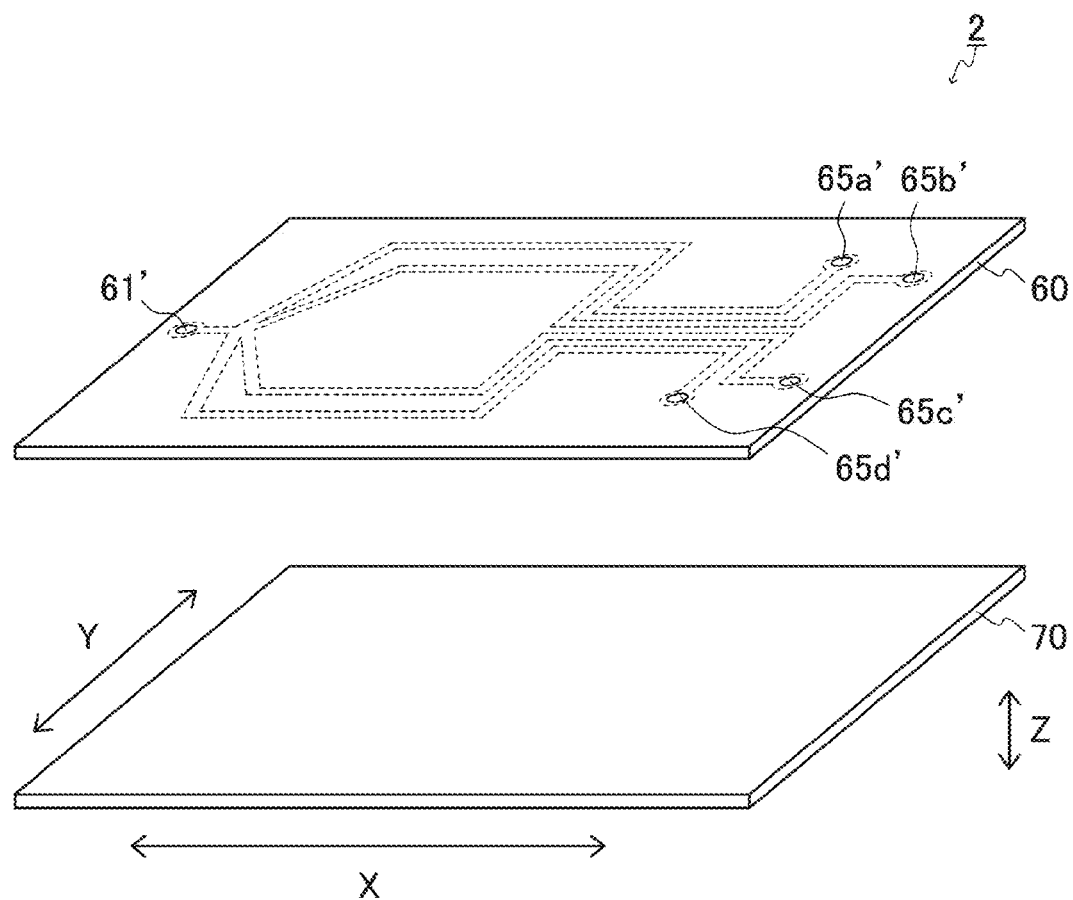
FIG. 2A is a perspective view showing another example of a micro-device.
Figure 2B:
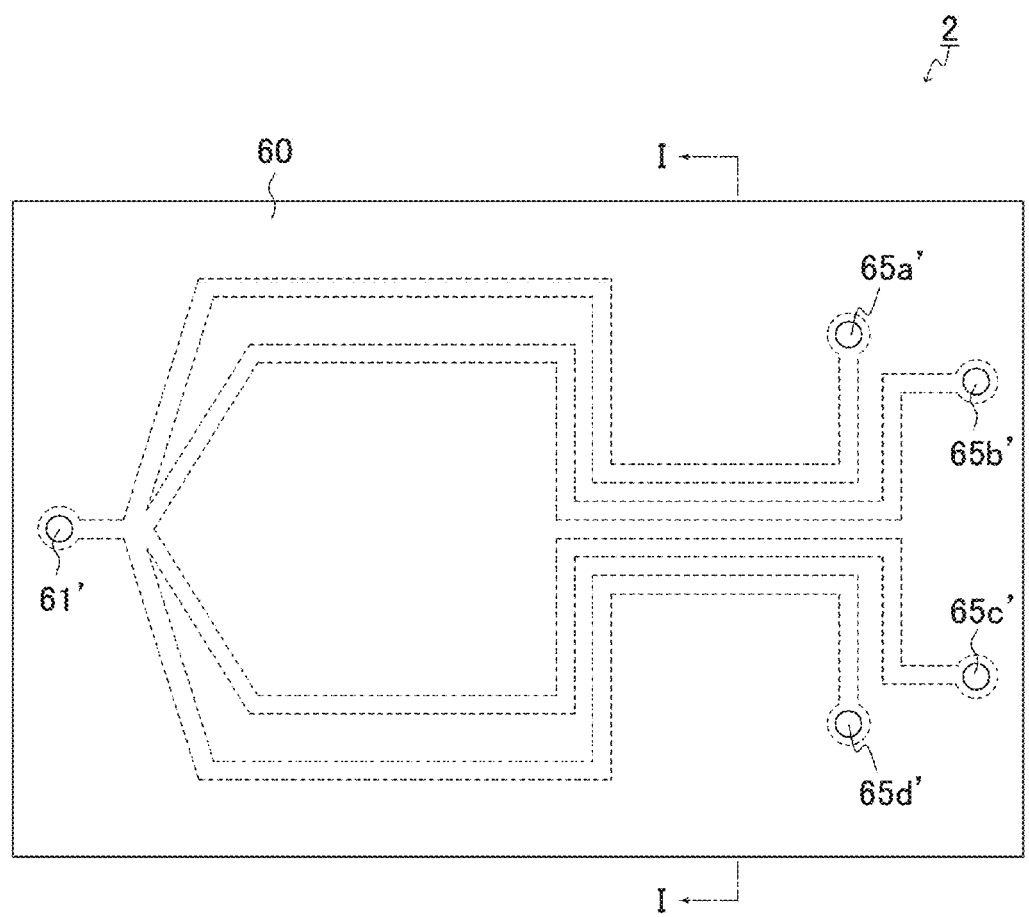
FIG. 2B is a top view showing the another example of a micro-device.
Figure 2C:
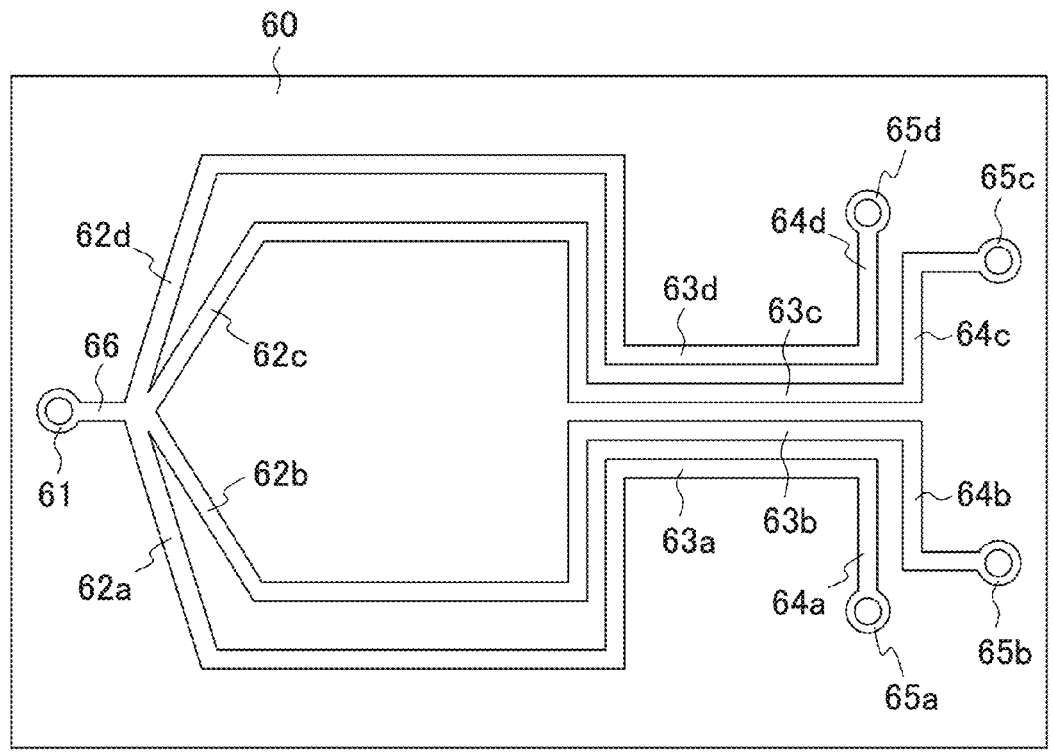
FIG. 2C is a bottom view showing an example of an upper substrate in the micro-device.
Figure 2D:
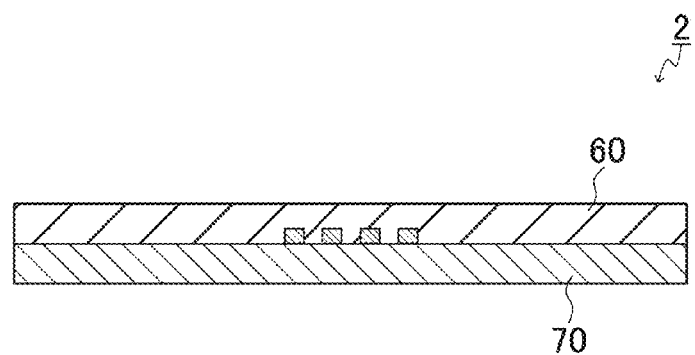
FIG. 2D is a cross-sectional view showing the another example of a micro-device.

FIGS. 2A to 2D show an example of the micro-device. FIG. 2A is a perspective view showing a micro-device 2 in the state of separating into an upper substrate 60 and a lower substrate 70 which configure the micro-device 2. FIG. 2B is a top view of the micro-device 2. FIG. 2C is a bottom view of the upper substrate 60, i.e., a drawing of the surface of the upper substrate 60 on which the lower substrate 70 is laminated. FIG. 2D is a cross-sectional view taken along the line I-I of FIG. 2B.

As shown in FIGS. 2A and 2B, the upper substrate 60 is provided with a through hole 61' as an inlet and through holes 65a' to 65d' as air vents. As shown in FIG. 2C, in the lower surface of the upper substrate 60, an introduction section 61 corresponding to the inlet 61', a first introduction flow channel 66, second introduction flow channels 62a to 62d branched from the downstream end of the first introduction flow channel 66, observation areas 63a to 63d, discharge flow channels 64a to 64d, and exhaust sections 65a to 65d are linked and formed as a concave portion.

Hereinafter, each space formed by linking the inlet, the introduction section, the first introduction flow channel, the second introduction flow channel, the observation area, the discharge flow channel, the exhaust section, and the air vent is referred to as a "lane", and the name of each lane is represented by the reference numeral of each second introduction flow channel. That is, for example, a space formed by linking an inlet 61', an introduction section 61, a first introduction flow channel 66, a second introduction flow channel 62a, an observation area 63a, a discharge flow channel 64a, an exhaust section 65a, and an air vent 65a' is referred to as a lane 62a.

The size of the micro-device 2 is not particularly limited and can be shown as follows, for example.
Overall Size
  Width (Length in an arrow X direction in FIG. 2A): e.g., 30 to 40 mm
  Length (Length in an arrow Y direction in FIG. 2A): e.g., 30 to 40 mm
  Thickness (Length in an arrow Z direction in FIG. 2A): e.g., 1 to 3 mm
Upper substrate 60
  Thickness: e.g., 0.8 to 2.8 mm
  Depth of concave portion: e.g., 17 μm
Inlet
  Diameter: e.g., 0.75 mm
Introduction Flow Channel
  Length: e.g., 50 mm
First introduction flow channel: e.g., 2 mm
Second introduction flow channel: e.g., 3 to 5 cm
Observation Area
  Length: e.g., 8 mm
Discharge Flow Channel
  Length: e.g., 2 to 5 mm
Exhaust Section
  Diameter: e.g., 1.5 mm The micro-device 2 includes a reagent section, for example. The position of the reagent section is not particularly limited. The reagent section preferably includes at least the observation area, more preferably includes a range from the position downstream from the first introduction flow channel (for example, the middle of the second introduction flow channel) to the exhaust section, for example.

In the micro-device 2, the introduction volume of the antimicrobial drug solution into each flow channel is not particularly limited and is, for example, 0.25 to 1 μL per a lane.

In the micro-device 2, the introduction volume of the bacterial suspension to be inspected is not particularly limited and is, for example, 9 to 10 μL. In the micro-device 2, the introduction density of bacteria in the bacterial suspension to be inspected is not particularly limited.

Each flow channel of the micro-device 2 has the same inlet and a different observation area. Therefore, according to the micro-device 2, for example, by placing a different antimicrobial drug in each flow channel and introducing, from the inlet, the same bacterial suspension to be inspected into each flow channel, the susceptibility of specific bacteria to be inspected to a plurality of antimicrobial drugs can be checked, for example. Moreover, according to the micro-device 2, for example, by placing the same antimicrobial drug with a different concentration in each flow channel and introducing the same bacterial suspension to be inspected into the inlet, the MIC (minimum inhibitory concentration) of the specific antimicrobial drug can be determined.

A specific example of the micro-device 2 can be, for example, in a form of placing a different antimicrobial drug in each of three lanes among the lanes 62a to 62d and using the remaining lane as a control of placing no antimicrobial drug. With this form, for example, the susceptibility of one kind of a bacterial suspension to be inspected to three kinds of antimicrobial drugs can be checked.

A method for inspecting susceptibility of a bacterial suspension to be inspected to a bacterial drug using the micro-device 2 is not particularly limited and can be described with reference to the above-mentioned example in FIG. 1 except that the bacterial suspension to be inspected is introduced from the inlet 61' into the micro-device 2.

(Third Embodiment)

A micro-device of the third embodiment is, as mentioned in the second embodiment, in a form of having the same inlet and different observation areas in a plurality of flow channels, for example. The micro-device of the third embodiment can be described with reference to the descriptions of the first and second embodiments unless otherwise specifically indicated.

In the micro-device, a plurality of flow channels have the same inlet, for example, and thus, in each observation area of the flow channels, inspections of the same bacterial suspension to be inspected on different antimicrobial drugs and/or inspections of the same bacterial suspension to be inspected on the same antimicrobial drug with different concentrations can be performed, for example.

Figure 10A:
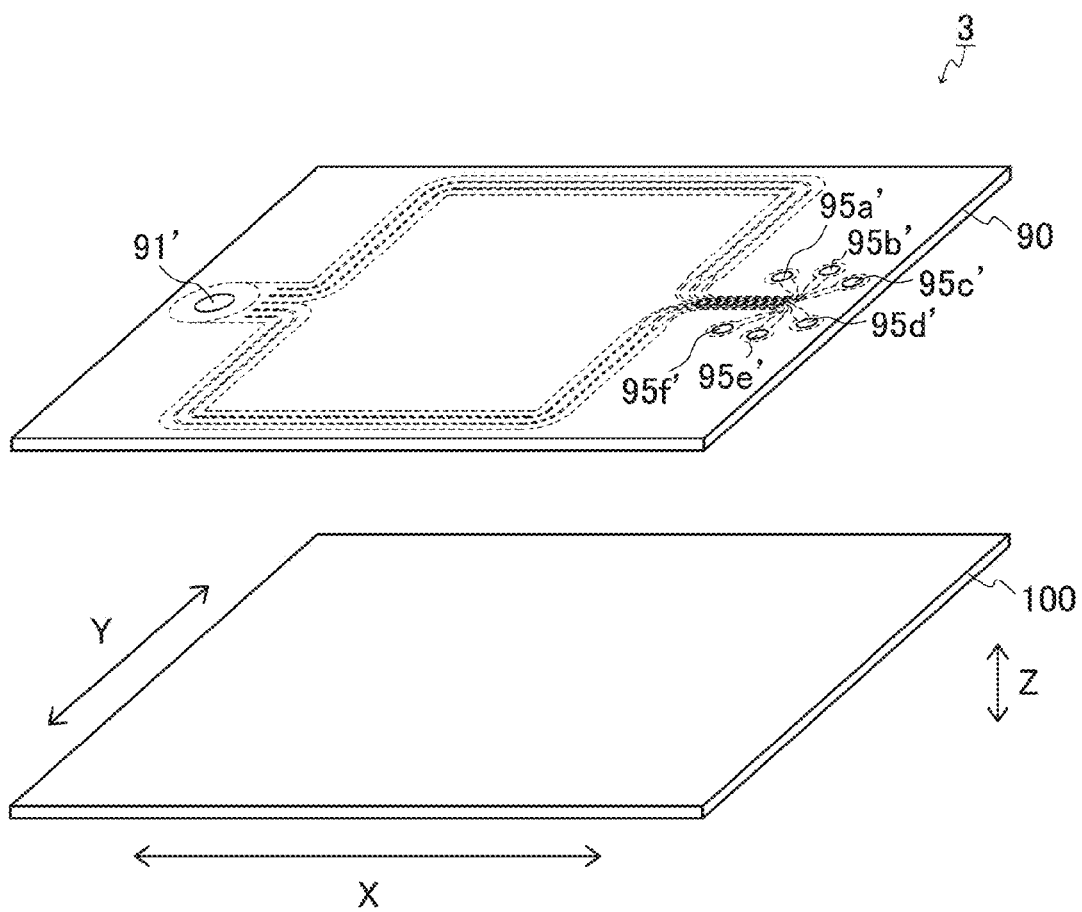
FIG. 10A is a perspective view showing yet another example of a micro-device.
Figure 10B:
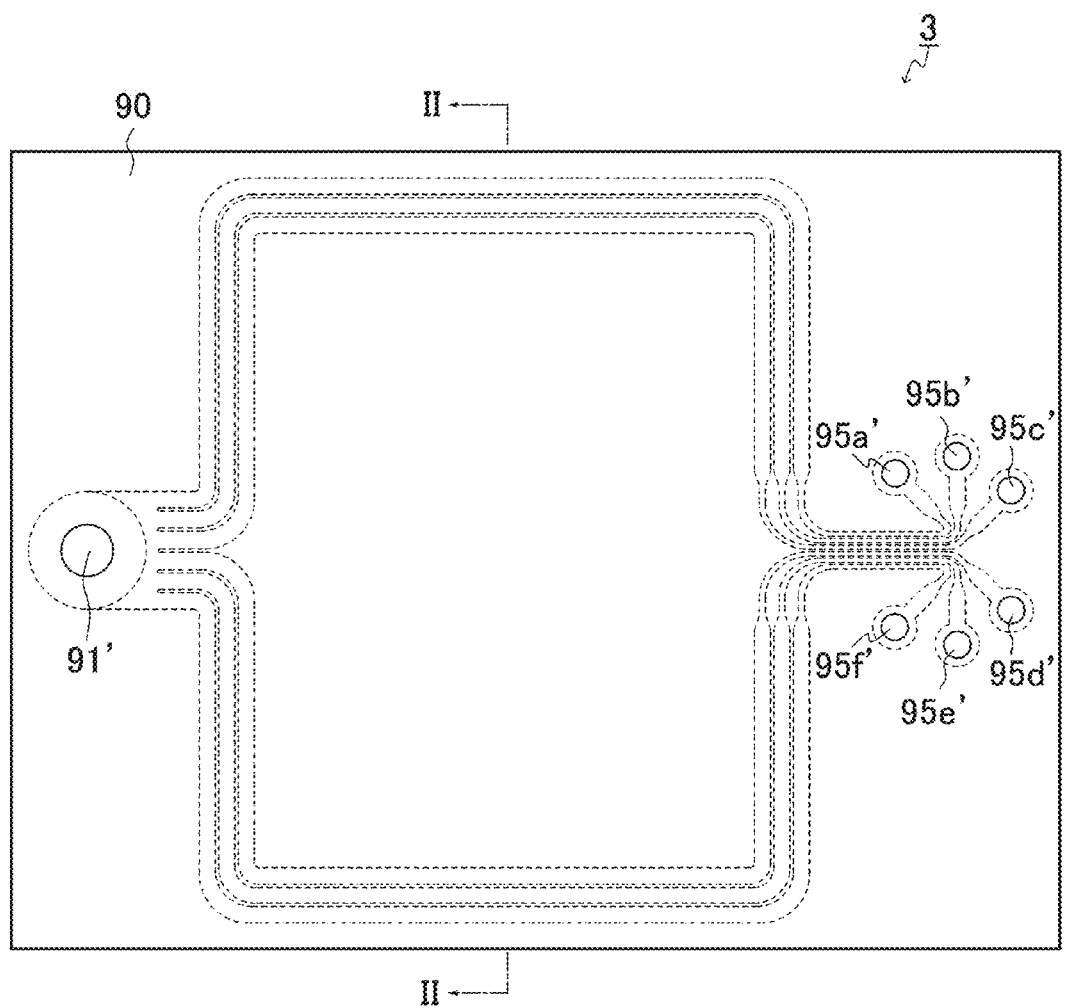
FIG. 10B is a top view showing the yet another example of a micro-device.
Figure 10C:
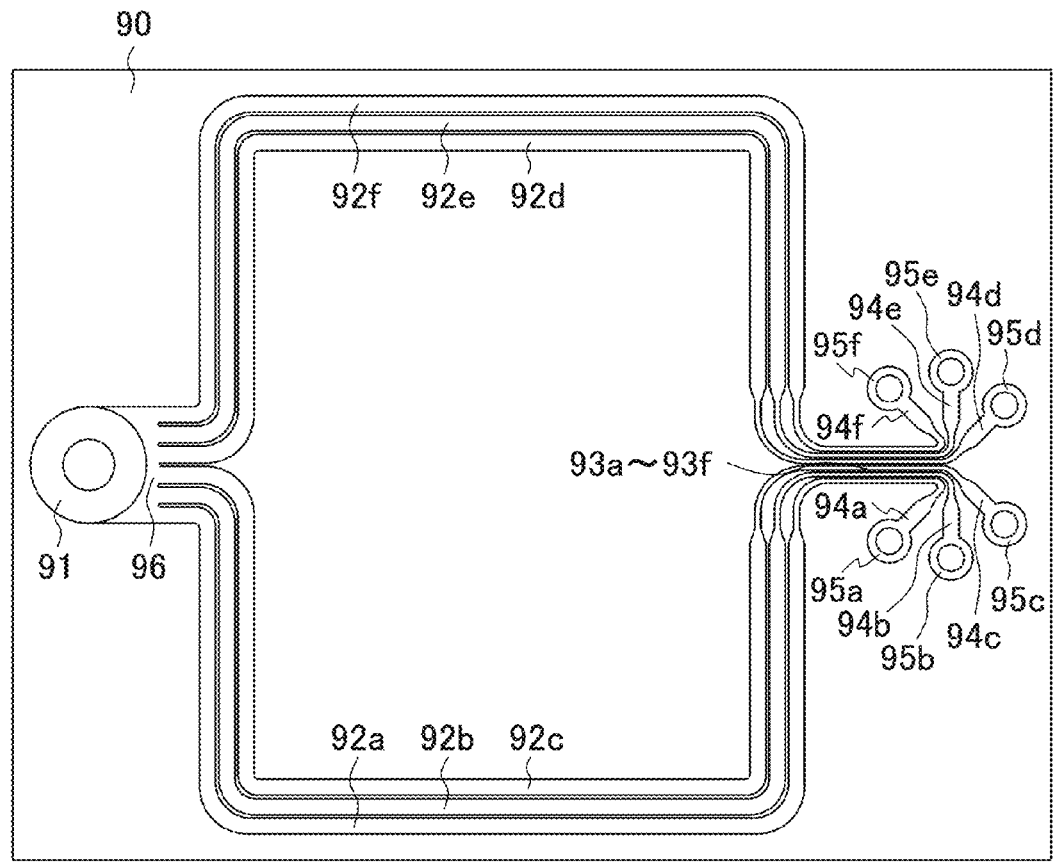
FIG. 10C is a bottom view showing the yet another example of an upper substrate in the micro-device.
Figure 10D:
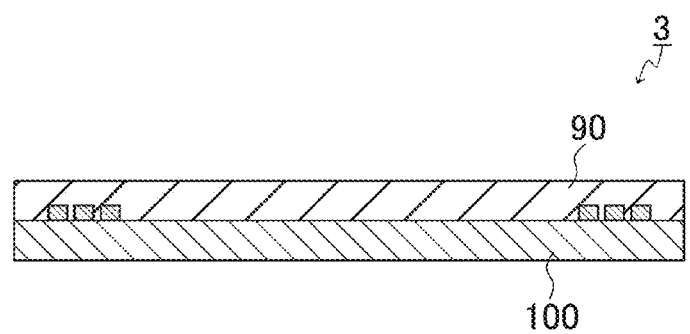
FIG. 10D is a cross-sectional view showing the yet another example of a micro-device.

FIGS. 10A to 10D show yet another example of the micro-device. FIG. 10A is a perspective view showing a micro-device 3 in the state of separating into an upper substrate 90 and a lower substrate 100 which configure the micro-device 3. FIG. 10B is a top view of the micro-device 3. FIG. 10C is a bottom view of the upper substrate 90, i.e., a drawing of the surface of the upper substrate 90 on which the lower substrate 10 is laminated. FIG. 10D is a cross-sectional view taken along the line II-II of FIG. 10B.

As shown in FIGS. 10A and 10B, the upper substrate 90 is provided with a through hole 91' as an inlet and through holes 95a' to 95f as air vents. As shown in FIG. 10C, in the lower surface of the upper substrate 90, an introduction section 91 corresponding to the inlet 91', a first introduction flow channel 96, second introduction flow channels 92a to 92f branched from the downstream end of the first introduction flow channel 96, observation areas 93a to 93f, discharge flow channels 94a to 94f, and exhaust sections 95a to 95f are linked and formed as a concave portion.

Hereinafter, each space formed by linking the inlet, the introduction section, the first introduction flow channel, the second introduction flow channel, the observation area, the discharge flow channel, the exhaust section, and the air vent is referred to as a "lane", and the name of each lane is represented by the reference numeral of each second introduction flow channel. That is, for example, a space formed by linking an inlet 91', an introduction section 91, a first introduction flow channel 96, a second introduction flow channel 92a, an observation area 93a, a discharge flow channel 94a, an exhaust section 95a, and an air vent 95a' is referred to as a lane 92a.

In the lanes of the micro-device 3, corners of the second introduction flow channels 92a to 92f are round. The widths of the flow channels of observation areas 93a to 93f are smaller than the widths of the second flow channels 92a to 92f and the widths of the discharge flow channels 92a to 92f. Moreover, in each lane, the lengths of the respective flow channels from the observation areas 93a to 93f to the exhaust sections 95a to 95f are the same.

The size of the micro-device 3 is not particularly limited and can be shown as follows, for example.

Overall Size
  Width (Length in an arrow X direction in FIG. 10A): e.g., 30 to 40 mm
  Length (Length in an arrow Y direction in FIG. 10A): e.g., 30 to 40 mm
  Thickness (Length in an arrow Z direction in FIG. 10A): e.g., 1 to 4 mm.
Upper substrate 60
  Thickness: e.g., 0.8 to 3 mm Depth of concave portion: e.g., 50 μm (inlet portion: e.g., 300 μm)
Inlet
  Diameter: e.g., 1 mm
Introduction Flow Channel
  Length: e.g., 25 to 35 mm
First Introduction Flow Channel
  Length: e.g., 2 mm
Second Introduction Flow Channel
  Length: e.g., 23 to 33 cm
  Width: e.g., 200 μm
Observation Area
  Length: e.g., 4 mm
  Width: e.g., 100 μm
Discharge Flow Channel
  Length: e.g., 2 to 3 mm
  Width: e.g., 500 μm
Exhaust Section
  Diameter: e.g., 1.5 mm The micro-device 3 includes a reagent section, for example. The reagent section is the same as in the above-mentioned second embodiment, for example.

In the micro-device 3, the introduction volume of the antimicrobial drug solution into each flow channel is not particularly limited and is, for example, 0.2 to 0.4 μL per a lane.

In the micro-device 3, the introduction volume of the bacterial suspension to be inspected is not particularly limited and is, for example, from 15 to 25 μL. In the micro-device 3, the introduction density of bacteria in the bacterial suspension to be inspected is not particularly limited.

Each flow channel of the micro-device 3 has the same inlet and a different observation area. Therefore, according to the micro-device 3, for example, the susceptibility of specific bacteria to be inspected to a plurality of antimicrobial drugs can be checked, or the MIC (minimum inhibitory concentration) of a specific antimicrobial drug can be determined, as in the above-mentioned second embodiment.

A specific example of the micro-device 3 can be, for example, in a form of placing a different antimicrobial drug in each of five lanes of the lanes 92a to 92f and using the remaining lane as a control of placing no antimicrobial drug. With this form, for example, the susceptibility of one kind of a bacterial suspension to be inspected to five kinds of antimicrobial drugs can be checked.

A method for inspecting susceptibility of a bacterial suspension to be inspected to an antimicrobial drug using the micro-device 3 is not particularly limited and can be described with reference to the above-mentioned example in FIG. 1 except that the bacterial suspension to be inspected is introduced from the inlet 91' into the micro-device 3.

Next, the inspection system of the present invention is, as mentioned above, a system for inspecting susceptibility of bacteria or fungi to an antimicrobial drug by the inspection method of the present invention, including: an incubation unit that incubates a micro-device having a flow channel containing a mixture of a bacterial suspension to be inspected and the antimicrobial drug; an image acquisition unit that acquires an image of an observation area in the flow channel of the micro-device; an information acquisition unit that acquires information on at least one of the number, the degree of sparseness or density, and the shape of bacteria or fungi in the image; and a determination unit that determines susceptibility of bacteria or fungi derived from the bacterial suspension to be inspected to the antimicrobial drug on the basis of the information.

The inspection system of the present invention can be, for example, an inspection device built by a computer system. The hardware structure of the system is not limited and may be, for example, a structure in which a storage device and input devices such as a keyboard, a mouse, and the like are connected to a CPU which is a control section, and a result output device, a display device (display) of displaying the input data and results, and the like further may be connected to the CPU, for example. Moreover, each unit may be a functional block that is realized by executing a predetermined program with a CPU of a computer. Therefore, for example, each composition unit may not be mounted as hardware and may be a network system.

The inspection system of the present invention further includes a fixing unit that sets up the micro-device, for example. The micro-device may be, for example, a disposable micro-device and may be replaced with every measurement and detection of a specimen. The inspection system has an inlet of introducing a specimen into the set micro-device, and the inlet may be identical to the inlet of the micro-device, for example. The inspection system includes a unit that automatically incubates a specimen introduced into the micro-device by temperature control or the like, for example. The inspection system further includes a unit that intermittently or continuously acquires automatically an image of an observation area of the micro-device, for example. The inspection system further has a unit that acquires data on the number, the degree of sparseness or density, or the shape of bacteria or fungi of the specimen or changes thereof from each image data and comparing the data with reference values, for example.

Figure 9:
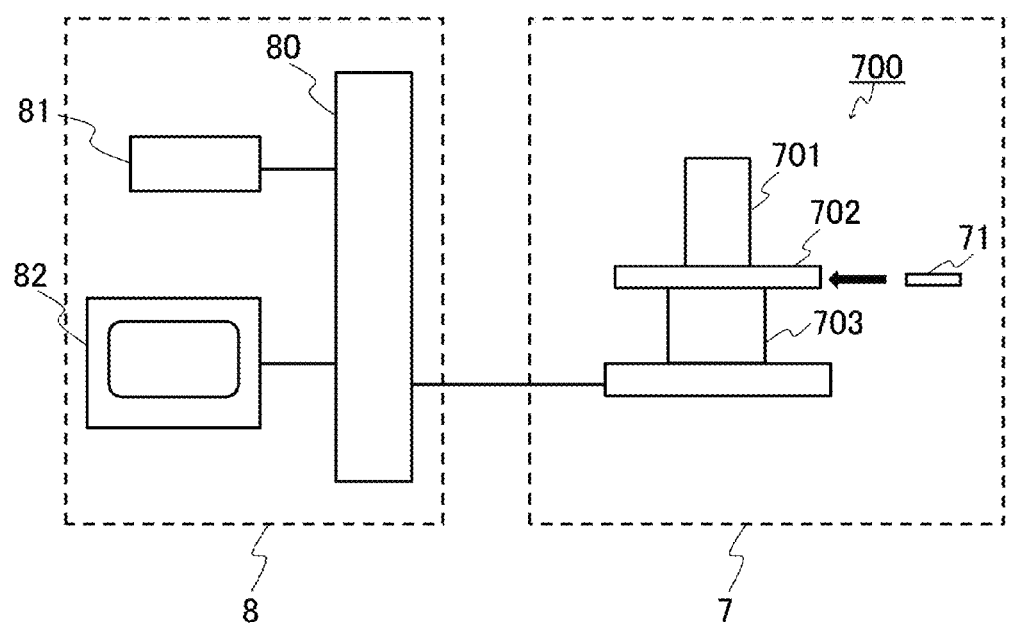
FIG. 9 is a block diagram showing an example of an inspection system of the present invention.

FIG. 9 shows an example of the configuration of the inspection system of the present invention. FIG. 9 is a schematic view, and the size, the form, and the like of the inspection system are not at all limited. FIG. 9 is merely an example, and the present invention is not limited thereby.

As shown in FIG. 9, the inspection system includes a measurement section 7 and an image processing section 8. The measurement section 7 includes a microscope 700. The microscope 700 contains a CCD camera 701 and includes a placement section 702 to which a micro-device 71 is set and a temperature control section 703 of controlling a temperature of the placement section 702. Although the microscope 700 is not shown, the microscope 700 includes components generally included in a microscope, such as a light source and the like, for example. The image processing section 8 includes a CPU 80, a storage section 81, and an output section 82. Examples of the storage section 81 include ROM, HDD, and HD. Examples of the output section 82 include a monitor and a printer.

According to the inspection system, the inspection method of the present invention can be carried out as follows, for example. First, a micro-device 71 is set in a placement section 702 of a microscope 700 in a measurement section 7. The micro-device 71 may be a micro-device into which a mixture of a bacterial suspension to be inspected and an antimicrobial drug has been previously introduced or a micro-device into which only an antimicrobial drug has been previously introduced. In the case of the micro-device into which only an antimicrobial drug has been introduced, the bacterial suspension to be inspected may be introduced after setting the micro-device in the placement section 702. Then, the micro-device 71 set in the placement section 702 is incubated by controlling a temperature in the placement section 702 by a temperature control section 703.

An image of an observation area of the micro-device 71 is taken by the CCD camera 701 of the microscope 700 and is output as a signal. The image can be taken intermittently or continuously. At that time, it is preferred that the measurement section 7 further includes a control section of controlling taking an image. The control section can be, for example, a CPU. Then, the output signal is input into a CPU 80 of the image processing section 8. When the signal is subjected to arithmetic processing by the CPU 80, data obtained after the arithmetic processing is output to an output section 82 and stored in a storage section 81.

By subjecting the signal output from the measurement section 7 to arithmetic processing by the CPU 80, data showing changes in the number, the degree of sparseness or density, and/or the shape of bacteria or fungi may be calculated, and further, the calculated data may be compared with reference values which has been previously set, to determine the susceptibility to an antimicrobial drug, for example.

EXAMPLES

The examples of the present invention are described below. The present invention, however, is not limited by the following examples.

Example 1

(1) Micro-device

A micro-device 1 shown in FIG. 1 was produced as follows. In the micro-device 1, an upper substrate 10 was made of PDMS, and a lower substrate 20 was made of glass. The size of the micro-device 1 was as follows.
Overall length (Y direction): 30 mm
Overall width (X direction): 40 mm
Overall thickness (Z direction): 2 to 3 mm
Depth of concave portion of upper substrate: 17 μm
Diameter of inlet: 0.75 mm
Length of introduction flow channel: 10 to 15 mm
Width of introduction flow channel: 0.1 mm
Length of observation area: 2 to 5 mm
Width of each flow channel of observation area: 0.1 mm
Length of discharge flow channel: 10 to 13 mm
Width of discharge flow channel: 0.1 mm
Diameter of exhaust section: 1 mm
Diameter of through hole of upper substrate: 0.75 mm
 (1-1) Production of Template
1) A cover glass with 40 mm×50 mm (No. 5, thickness: 1 mm, Matsunami Glass Ind., Ltd.) or a silicon wafer (3 inch, Ferrotec Co.) was spin-coated with a coating agent (trade name: OmniCoat, MicroChem) at 4000 rpm for 10 seconds and then baked at 180° C. for 1 minute.
2) A resultant object was spin-coated with a photoresist (SU8-25, MicroChem) at 2000 rpm for 30 seconds so as to have a film thickness of 16 to 17 μm.
3) The object was pre-baked at 65° C. for 3 minutes and 95° C. for 7 minutes.
4) The object was exposed to light in a micro-pattern by a maskaligner (trade name: ES20, Nanomeric Technology Inc.) for 11 seconds.
5) After the exposure to light, the object was baked at 65° C. for 1 minute and 95° C. for 3 minutes.
6) The object was subjected to development for 2 minutes by a SU8-Developer (trade name, MicroChem Corp.).
7) The object was hard-baked at 180° C. for 30 minutes in order to hardly bake.
8) The object was spin-coated with 0.84 wt % Cytop809ME (trade name, Asahi Glass Co., Ltd,) at 4000 rpm and treated at 180° C. for 1 hour in order to cause PDMS described below to be easily removed.
 (1-2) Molding of PDMS Flow Channel
1) Polydimethylsiloxane (PDMS) (trade name: Silpot 184, Dow Corning Toray Co., Ltd.) and a polymerization catalyst were mixed at a weight ratio of 10:1, and a resultant mixture was deaerated for 30 minutes.
2) The mixture was dipped in a mold, which was then sintered at 100° C. for 30 minutes.
 (1-3) Lamination of Glass Substrate and PDMS
1) The solidified PDMS base material was removed and placed in a reactive ion etching device (trade name: RIE-10NR, Samco) together with a cover glass (No. 1, thickness: 0.12 to 0.17 mm, Matsunami Glass Ind., Ltd.) previously washed with ethanol.
2) The cover glass and the PDMS base material were exposed to oxygen plasma at an oxygen flow rate of 100 standard cubic/minute (sccm), a pressure of 50 Pa, and an RF power of 30 W for 20 seconds.
3) The plasma-treated surface of the cover glass and the plasma-treated surface of the PDMS base material were laminated and bonded to each other.
4) Through holes as an inlet(s) and an air vent(s) were bored in the bonded laminate with a puncher (trade name: BP-15F, Kai Industries Co., Ltd.).
 (2) Preparation of Antimicrobial Drug Solution
Each of three kinds of antimicrobial drugs shown below was mixed in phosphate buffered saline (PBS, 10 mmol/L, pH7.2 to pH7.4) so as to have the following concentrations. Thus, antimicrobial drug solutions were prepared. Amikacin (trade name: AMK, Sigma)
640, 320, 160, 80 μg/mL
Ciprofloxacin (trade name: CPFX, Tokyo Chemical Industry Co., Ltd.)
80, 40, 20, 10 μg/mL
Imipenem/Cilastatin (trade name: IPM, Banyu Pharmaceutical Co. Ltd.)
320, 160, 80, 40 μg/mL (IPM concentration)
 (3) Preparation of Bacterial Suspension to be Inspected
*Pseudomonas aeruginosa* was pre-cultured at 37° C. for 24 hours using a Mueller-Hinton Agar (Becton, Dickinson and Company) plate. A colony was suspended in a Mueller-Hinton broth so as to have MacFarland=0.5 (OD600=0.132). As *Pseudomonas aeruginosa*, multi-drug resistant strains #2 and #5 (available from BML) and an S1 strain (susceptibility strain, available from BML) were used.
 (4) Incubation
The antimicrobial drug solution obtained in the (2) above and the culture solution obtained in the (3) above were mixed at a volume ratio of 1 9, and 1 μL of a resultant mixture was injected into each inlet of a micro-device 1. As a control, sterile water as a substitute for the antimicrobial drug solution and the culture solution were mixed at a volume ratio of 1:9, and 1 μL of a resultant mixture was injected into an inlet of the micro-device 1. Then, the micro-device 1 was placed in a petri dish, and the petri dish was placed in an airtight container. Kimwipe (Trade Mark) containing water was placed in each of the petri dish and the airtight container. The airtight container was placed in an incubator at 37° C. and incubated for 3 hours. The relative humidity of each of the airtight container and the petri dish was 97%.

(5) Determination

The micro-device 1 was taken out of the airtight container, and an increase or decrease in the amount of bacteria and a change in shape relative to the control in an observation area was checked by a microscope, and the MIC (minimum inhibitory concentration) was determined.

On the other hand, the MIC of each of AMK, CPFX, and IPM to the same *Pseudomonas aeruginosa* was measured by a broth microdilution method according to the CLSI standards (standard method).

Figure 3:
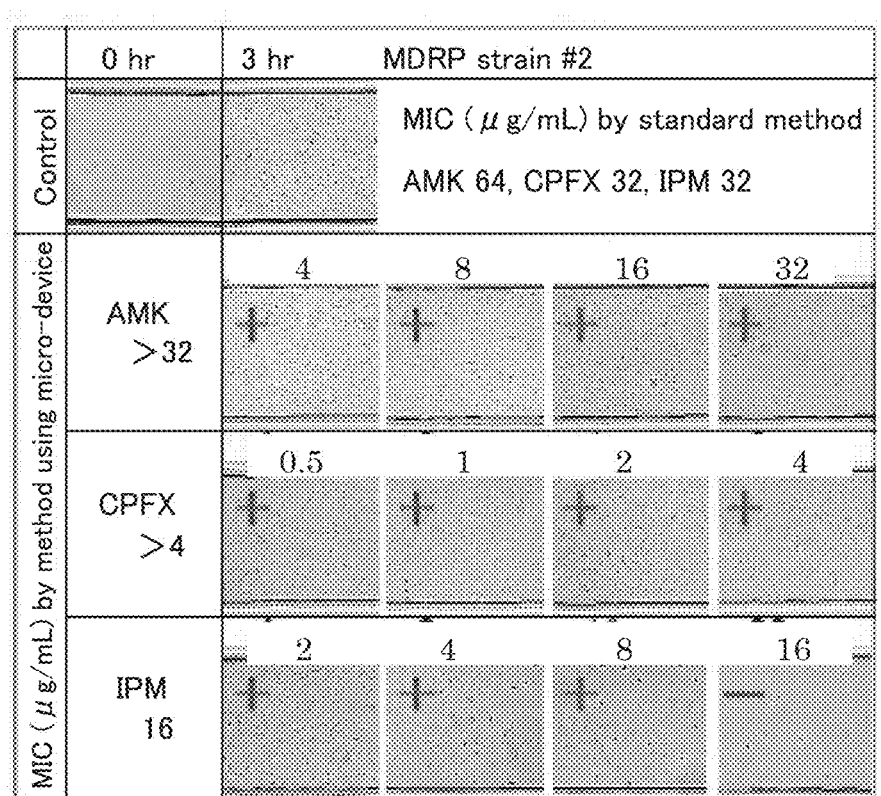
FIG. 3 shows microscope photographs of *Pseudomonas aeruginosa* in an example of the present invention.

FIG. 3 shows microscope photographs of the #2 strain of *Pseudomonas aeruginosa* after the incubation. In FIG. 3, the numbers in the photographs of AMK, CPFX, and IPM show the final concentrations (μg/mL) of the respective antimicrobial drugs, "+" shows that the #2 strain had grown compared with the control (0 hr), and "−" shows that the growth of the #2 strain was the same as the control (0 hr), and the growth is suppressed. As shown in FIG. 3, the results of the method using the micro-device showed that the MIC of AMK to the #2 strain of *Pseudomonas aeruginosa* was 32 μg/mL or more, the MIC of CPFX to the same was 4 μg/mL or more, and the MIC of the IPM to the same was 16 μg/mL. On the other hand, the results of the standard method showed that the MIC of the AMK was 64 μg/mL, the MIC of the CPFX was 32 μg/mL, and the MIC of the IPM was 32 μg/mL. The MIC of the IPM by the standard method was two times more than the MIC of IPM by the method using the micro-device. However, each MIC was determined as the same, Resistance (R), based on the break point of CLSI as an indicator.

Figure 4:
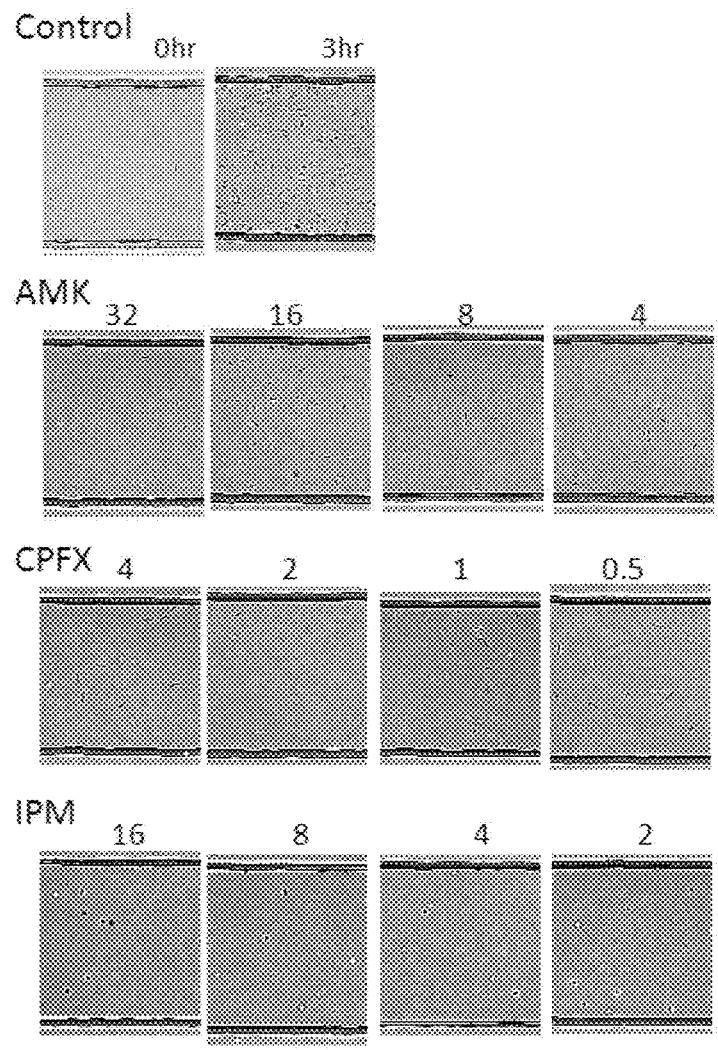
FIG. 4 show microscope photographs of another *Pseudomonas aeruginosa* in the example of the present invention.

FIG. 4 shows microscope photographs of the S1 strain of *Pseudomonas aeruginosa* after the incubation. In FIG. 4, the numbers in the photographs of AMK, CPFX, and IPM show the final concentrations (μg/mL) of the respective antimicrobial drugs. As shown in FIG. 4, at each concentration of each antimicrobial drug, the growth as in a control (3 hr) was not shown. Thus, the results showed that the S1 strain showed susceptibility to each antimicrobial drug.

Figure 5:
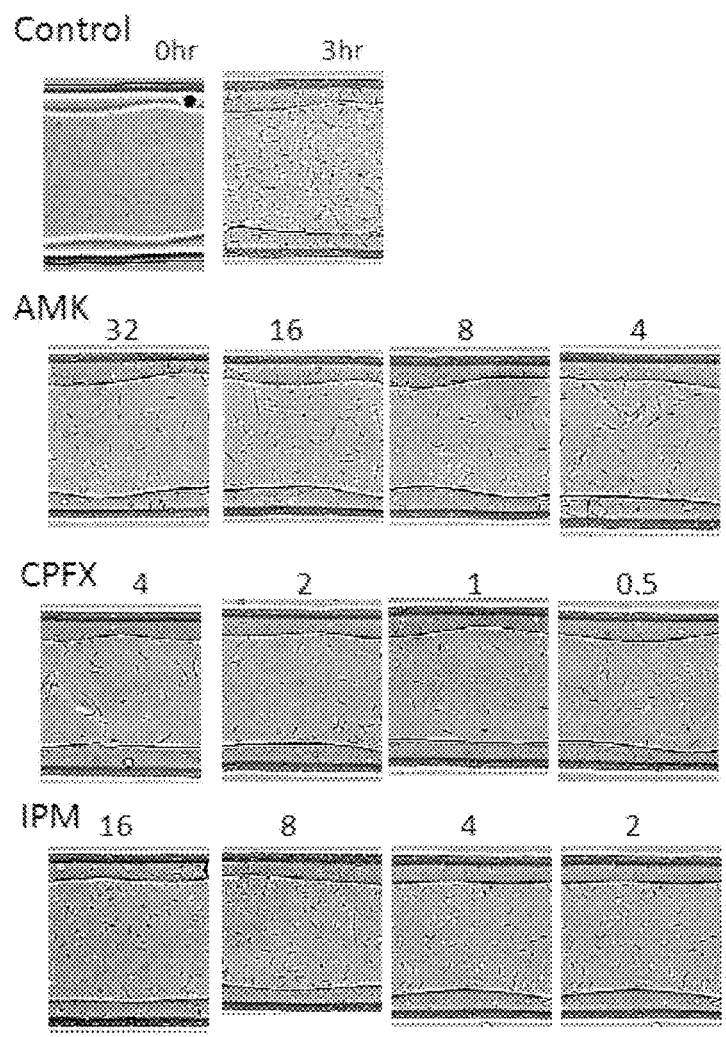
FIG. 5 show microscope photographs of yet another *Pseudomonas aeruginosa* in the example of the present invention.

FIG. 5 shows microscope photographs of the #5 strain (MDRP) of *Pseudomonas aeruginosa* after the incubation. In FIG. 5, the numbers in the photographs of AMK, CPFX, and IPM show the final concentrations (μg/mL) of the respective antimicrobial drugs. As shown in FIG. 5, at each concentration of each antimicrobial drug, the growth was promoted compared with a control (0 hr). Thus, the results showed that the #5 strain showed a resistance to each antimicrobial drug.

Example 2

(1) Micro-device

A micro-device shown in FIG. 2 was produced in the same manner as in Example 1. In the micro-device, an upper substrate was made of PDMS, and a lower substrate was made of glass. The size of the micro-device 2 was as follows.
Overall length (Y direction): 40 mm
Overall width (X direction): 30 mm
Overall thickness (Z direction): 2 mm
Depth of concave portion of upper substrate 60: 17 μm
Diameter of inlet: 0.75 mm
Diameter of introduction section: 3 mm
Length of introduction flow channel: 30 to 40 mm
First introduction flow channel: 1 to 2 mm
Second introduction flow channel: 28 to 39 mm
Width of introduction flow channel: 0.3 to 0.5 mm
Length of observation area: 8 mm
Width of observation area: 0.5 mm
Length of discharge flow channel: 2 to 4 mm
Width of discharge flow channel: 0.5 mm
Diameter of exhaust section: 1.5 mm Each of Amikacin (trade name: AMK, Sigma), Ciprofloxacin (trade name: CPFX, Tokyo Chemical Industry Co., Ltd.), and Imipenem/Cilastatin (trade name: IPM, Banyu Pharmaceutical Co. Ltd.) was dissolved in PBS so as to each have a concentration of 2 to 4 mg/mL. Each resultant solution was then further diluted with 100% ethanol. Thus, antimicrobial drugs with the respective predetermined concentrations were prepared (AMK: 160 μg/mL, CPFX: 20 μg/mL, IPM: 80 μg/mL). Then, 0.25 μL of each antimicrobial drug was injected into each exhaust section of the micro-device 2, and the micro-device 2 was dried for about 15 minutes at room temperature.

(2) Determination

The incubation and determination were performed in the same manner as in Example 1 except that about 10 μL of a bacterial suspension to be inspected, prepared in the same manner as in Example 1, was injected into a common inlet.

Figure 7:
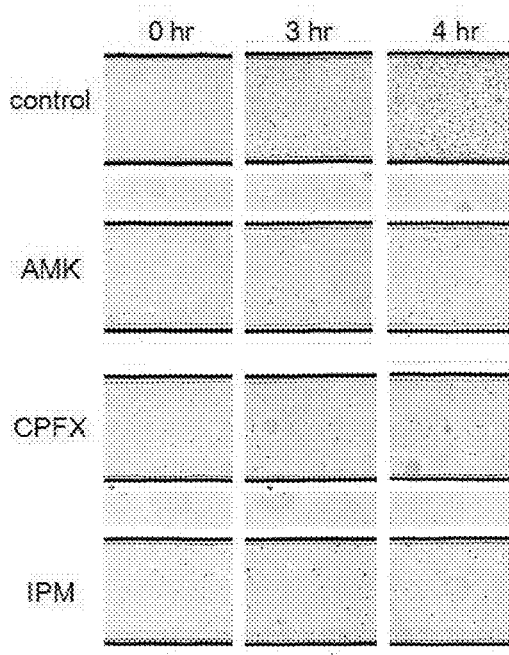
FIG. 7 show microscope photographs of *Pseudomonas aeruginosa* in an example of the present invention.

FIG. 7 shows microscope photographs of the S1 strain (susceptibility strain) of *Pseudomonas aeruginosa* after the incubation. As shown in FIG. 7, according to the method using the micro-device 2, the growth of the S1 strain of *Pseudomonas aeruginosa* according to the incubation time was found in the flow channel with no addition of antimicrobial drug (control). However, the growth was not found in each flow channel with the addition of each antimicrobial drug.

Figure 8:
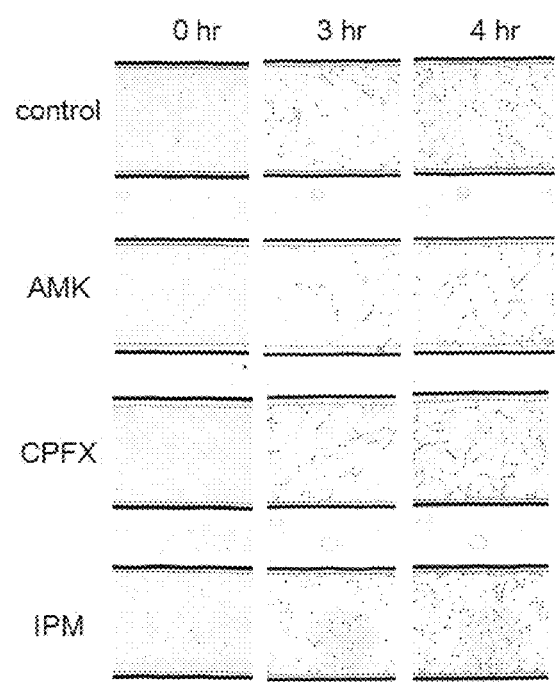
FIG. 8 is microscope photographs of another *Pseudomonas aeruginosa* in the example of the present invention.

FIG. 8 shows microscope photographs of the #5 strain (MDRP) of *Pseudomonas aeruginosa* after the incubation. As shown in FIG. 8, according to the method using the micro-device 2, when each antimicrobial drug was added, the growth of the #5 strain of *Pseudomonas aeruginosa* according to the incubation time was found in the case where each antimicrobial drug was added as in the case where the antimicrobial drug was not added (control).

Example 3

Figure 6:
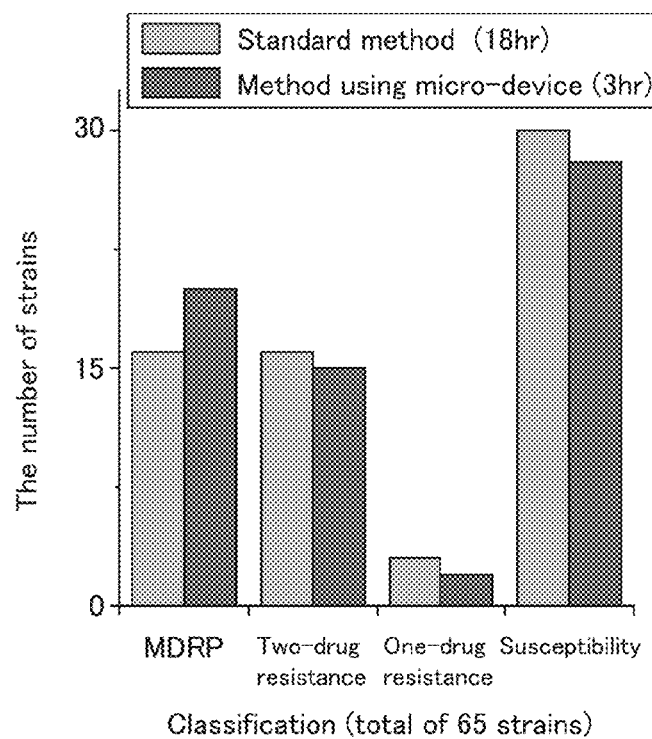
FIG. 6 is a graph showing a classification of 65 kinds of *Pseudomonas aeruginosa* strains in an example of the present invention.

65 kinds of *Pseudomonas aeruginosa* strains were treated with AMK, CPFX, and IPM in the same manner as in Example 2 and classified into multi-drug resistance (three-drug resistance), two-drug resistance, one-drug resistance, and susceptibility (susceptibility to three drugs). Moreover, 65 kinds of *Pseudomonas aeruginosa* strains were classified into the resistances and the susceptibility by the standard method described in Example 1. FIG. 6 shows the results thereof. FIG. 6 is a graph showing the number of strains classified into each of the resistances and the susceptibility among the 65 strains of *Pseudomonas aeruginosa*. As shown in FIG. 6, the same classification results as in the case of using the standard method were obtained by the method using the micro-device of the present example. The results showed that according to the method using the micro-device of the present invention, the resistance and the susceptibility can be determined in a really short time (3 hours) compared with the standard method that requires a long time to determine.

INDUSTRIAL APPLICABILITY

As described above, according to the present invention, the susceptibility of bacteria or fungi to an antimicrobial drug can be easily and rapidly checked by incubating a mixture of an antimicrobial drug and a bacterial suspension to be inspected in a flow channel of the micro-device and observing an observation area of the flow channel by, for example, a microscope.

Moreover, according to the inspection system of the present invention, the inspection method of the present invention can be easily performed. Therefore, the present invention is really useful in clinical inspection, environmental test, and the like. Specifically, in the clinical inspection, for example, an appropriate antimicrobial drug for bacteria and fungi to be inspected can be promptly selected. Thus, effects such as an improvement in lifesaving rate, a reduction in amount of an unnecessary drug to be used, and the like are expected, and in the long run, there is a possibility of suppressing an increase in the number of resistant bacteria.

EXPLANATION OF REFERENCE NUMERALS

| | |
|---|---|
| 1, 2, 3 | micro-device |
| 10, 60, 90 | upper substrate |
| 20, 70, 100 | lower substrate |
| 11', 21', 31', 41', 51', 61', 91' | inlet |
| 11, 21, 31, 41, 51, 61, 91 | introduction section |
| 12, 22, 32, 42, 52, 62, 92 | introduction flow channel |
| 13, 23, 33, 43, 53, 63, 93 | observation area |
| 14, 24, 34, 44, 54, 64, 94 | discharge flow channel |
| 15, 25, 35, 45, 55, 65, 95 | exhaust section |
| 15', 25', 35', 45', 55', 65', 95' | air vent |
| 7 | measurement section |
| 700 | Microscope |
| 701 | CCD camera |
| 702 | placement section |
| 703 | temperature control section |
| 71 | micro-device |
| 8 | image processing section |
| 80 | CPU |
| 81 | storage section |
| 82 | output section |

The invention claimed is:

1. A method for inspecting a susceptibility of bacteria or fungi to an antimicrobial drug using a micro-device having a plurality of flow channels, comprising:
    providing a suspension to be inspected to a micro-device having a plurality of flow channels in which an antimicrobial drug already is present, the respective flow channels differing from one another in at least one selected from the identity and the concentration of the antimicrobial drug;
    incubating a mixture of the antimicrobial drug and a suspension to be inspected in the plurality of flow channels of the micro-device, and
    detecting with a microscope, bacteria or fungi derived from the suspension to be inspected in an observation area of each of the plurality of flow channels of the micro-device, wherein, in the micro-device,
    the antimicrobial drug is placed in each of the plurality of flow channels before introducing the suspension to be inspected into the flow channels,
    the plurality of flow channels have a common inlet,
    each of the flow channels comprises the common inlet, the observation area, and an exhaust section in this order,
    the plurality of flow channels are in parallel and positioned to be in a field of view of the microscope in the observation areas,
    the observation areas of the plurality of flow channels all have the same width and the same length,
    in each of the flow channels, a length of a part extending from an exhaust section-side end of the observation area to the exhaust section is shorter than that of a part extending from a common inlet side end of the observation area to the common inlet, and
    wherein, in the incubating step, the suspension to be inspected is introduced into each of the flow channels via the common inlet of the micro-device, and
    all of the observation areas of the plurality of flow channels are observable within a field of view of the microscope at the same time and all of the observation areas of the plurality of flow channels are inspected with the microscope at the same time.

2. The method according to claim 1, wherein
    in the detecting step, at least one of a number and a shape of bacteria or fungi derived from the suspension to be inspected in each of the observation areas is observed.

3. The method according to claim 1, wherein
    a depth of each of the flow channels is from 10 to 25 μm.

4. The method according to claim 1, wherein
    the detecting step is performed after the incubating step.

5. A method for inspecting a susceptibility of bacteria or fungi to an antimicrobial drug using a micro-device having a plurality of flow channels, comprising:
    providing a suspension to be inspected to a micro-device having a plurality of flow channels in which an antimicrobial drug already is present, the respective flow channels differing from one another in at least one selected from the identity and the concentration of the antimicrobial drug;
    incubating a mixture of the antimicrobial drug and the suspension to be inspected in the plurality of flow channels of the micro-device; and
    detecting with a microscope, bacteria or fungi derived from the suspension to be inspected in an observation area of the plurality of flow channels of the micro-device,
    wherein, in the micro-device,
    the plurality of flow channels have a common inlet,
    each of the flow channels comprises the common inlet, the observation area, and an exhaust section in this order,
    the plurality of flow channels are in parallel and positioned to be in a field of view of the microscope in the observation areas,
    the observation areas of the plurality of flow channels all have the same width and the same length,
    in each of the flow channels, a length extending from an exhaust section-side end of the observation area to the exhaust section is shorter than a part extending from a common inlet side end of the observation area to the common inlet, and
    wherein, before the incubating step, the suspension to be inspected is introduced into each of the flow channels via the common inlet of the micro-device, and
    all of the observation areas of the plurality of flow channels are observable within a field of view of the microscope at one time and all of the observation areas of the plurality of flow channels are inspected with the microscope at the same time.

6. The method according to claim 5, wherein
    in the detecting step, at least one of a number and a shape of bacteria or fungi derived from the suspension to be inspected in each of the observation areas is observed.

7. The method according to claim 5, wherein
    a depth of each of the flow channels is from 10 to 25 μm.

8. The method according to claim 5, wherein
    the detecting step is performed before or after the incubating step.

9. The method according to claim 1, wherein
    in the respective flow channels, the lengths of the parts extending from the exhaust section-side ends of the observation areas to the exhaust sections are the same.

10. The method according to claim 1, wherein
in each of the flow channels, the observation area has a smaller width than the part extending from the common inlet side end of the observation area to the common inlet and the part extending from the exhaust section-side end of the observation area to the exhaust section.

11. The method according to claim 1, wherein
in the respective flow channels, lengths of the parts extending from the exhaust section-side ends of the observation areas to the exhaust sections are the same, and
in each of the flow channels, the observation area has a smaller width than the part extending from the common inlet side end of the observation area to the common inlet and the part extending from the exhaust section-side end of the observation area to the exhaust section.

12. The method according to claim 1, wherein
the antimicrobial drug is placed by introducing an antimicrobial drug solution containing the antimicrobial drug to the exhaust section and drying the antimicrobial drug solution.

13. The method according to claim 1, wherein
one of the plurality of flow channels is a control flow channel in which the antimicrobial drug is not placed.

14. The method according to claim 13, wherein
in the detecting step, at least one of a number and a shape of bacteria or fungi derived from the suspension to be inspected in the observation area of the control flow channel and at least one of a number and a shape of bacteria or fungi derived from the suspension to be inspected in each of the observation areas of the flow channels in which the antimicrobial drug is placed are observed.

15. The method according to claim 5, wherein
in each of the respective ones of the plurality of flow channels, lengths of the parts extending from the exhaust section-side ends of the observation areas to the exhaust sections are the same.

16. The method according to claim 1, wherein
in each of the flow channels, the observation area has a smaller width than the part extending from the common inlet side end of the observation area to the common inlet and the part extending from the exhaust section-side end of the observation area to the exhaust section.

17. The method according to claim 5, wherein
in each of the respective ones of the plurality of flow channels, lengths of the parts extending from the exhaust section-side ends of the observation areas to the exhaust sections are the same, and
in each of the flow channels, the observation area has a smaller width than the part extending from the common inlet side end of the observation area to the common inlet and the part extending from the exhaust section-side end of the observation area to the exhaust section.

18. The method according to claim 5, wherein
the antimicrobial drug is placed by introducing an antimicrobial drug solution containing the antimicrobial drug to the exhaust section and drying the antimicrobial drug solution.

19. The method according to claim 5, wherein
one of the plurality of flow channels is a control flow channel in which the antimicrobial drug is not placed.

20. The method according to claim 19, wherein
in the detecting step, at least one of a number and a shape of bacteria or fungi derived from the suspension to be inspected in the observation area of the control flow channel and at least one of a number and a shape of bacteria or fungi derived from the suspension to be inspected in each of the observation areas of the flow channels in which the antimicrobial drug is placed are observed.

* * * * *